US009990381B2

(12) United States Patent
Eltoukhy et al.

(10) Patent No.: US 9,990,381 B2
(45) Date of Patent: Jun. 5, 2018

(54) BIOSENSORS FOR BIOLOGICAL OR CHEMICAL ANALYSIS AND SYSTEMS AND METHODS FOR SAME

(71) Applicant: ILLUMINA, INC., San Diego, CA (US)

(72) Inventors: Helmy A. Eltoukhy, Atherton, CA (US); Robert C. Kain, San Diego, CA (US); Wenyi Feng, San Diego, CA (US); Mark Pratt, Belmont, CA (US); Bernard Hirschbein, San Francisco, CA (US); Poorya Sabounchi, Atherton, CA (US)

(73) Assignee: ILLUMINA, INC., San Diego, CA (US)

( * ) Notice: Subject to any disclaimer, the term of this patent is extended or adjusted under 35 U.S.C. 154(b) by 327 days.

(21) Appl. No.: 14/552,673

(22) Filed: Nov. 25, 2014

(65) Prior Publication Data
US 2015/0079596 A1    Mar. 19, 2015

Related U.S. Application Data

(62) Division of application No. 13/833,619, filed on Mar. 15, 2013, now Pat. No. 8,906,320.

(60) Provisional application No. 61/625,051, filed on Apr. 16, 2012.

(51) Int. Cl.
G01N 21/64 (2006.01)
G06F 17/30 (2006.01)
G01N 33/68 (2006.01)

(52) U.S. Cl.
CPC ....... *G06F 17/303* (2013.01); *G01N 21/6486* (2013.01); *G01N 33/6875* (2013.01)

(58) Field of Classification Search
None
See application file for complete search history.

(56) References Cited

U.S. PATENT DOCUMENTS

| | | |
|---|---|---|
| 4,755,667 A | 7/1988 | Marsoner |
| 5,605,662 A | 2/1997 | Heller |
| 5,653,939 A | 8/1997 | Hollis |
| 5,672,881 A | 9/1997 | Striepe |
| 5,843,767 A | 12/1998 | Beattie |
| 5,846,708 A | 12/1998 | Hollis |
| 5,854,684 A | 12/1998 | Stabile |
| 5,872,623 A | 2/1999 | Stabile |
| 5,894,351 A | 4/1999 | Colvin |
| 5,942,775 A | 8/1999 | Yiannoulos |
| 5,965,452 A | 10/1999 | Kovacs |
| 6,111,248 A | 8/2000 | Melendez |
| 6,117,643 A | 9/2000 | Simpson |
| 6,122,042 A | 9/2000 | Wunderman |
| 6,197,503 B1 | 3/2001 | Vo Dinh |
| 6,317,207 B2 | 11/2001 | French |
| 6,323,944 B1 | 11/2001 | Xiao |
| 6,327,410 B1 * | 12/2001 | Walt ............... B01J 19/0046 359/900 |
| 6,403,970 B1 | 6/2002 | Hung |
| 6,440,722 B1 | 8/2002 | Knapp |
| 6,441,892 B2 | 8/2002 | Xiao |
| 6,448,064 B1 | 9/2002 | Vo Dinh |
| 6,458,547 B1 | 10/2002 | Bryan |
| 6,469,785 B1 | 10/2002 | Duveneck |
| 6,485,905 B2 | 11/2002 | Hefti |
| 6,566,805 B1 | 5/2003 | Tsai |
| 6,653,083 B2 | 11/2003 | Emoto |
| 6,686,150 B1 | 2/2004 | Blackburn |
| 6,693,269 B2 | 2/2004 | Shimizu |
| 6,743,581 B1 | 6/2004 | Vo Dinh |
| 6,784,982 B1 | 8/2004 | Blumenfeld |
| 6,844,563 B2 | 1/2005 | Emoto |
| 6,867,420 B2 | 3/2005 | Mathies |
| 6,867,851 B2 | 3/2005 | Blumenfeld |
| 6,899,137 B2 | 5/2005 | Unger |
| 6,905,834 B1 | 6/2005 | Simpson |

(Continued)

FOREIGN PATENT DOCUMENTS

| | | | |
|---|---|---|---|
| WO | WO 98/29736 A1 | 7/1998 | |
| WO | WO 00/04372 A1 | 1/2000 | |
| WO | WO-2012058096 A1 * | 5/2012 | ........ B01L 3/502715 |

OTHER PUBLICATIONS

JH Leamon, JM Rothberg. Cramming More Sequencing Reactions onto Microreactor Chips. Chem Rev 2007, vol. 107, p. 3367-3376.*
M Marguiles et al. Genome-sequencing in microfabricated high-density picolitre reactors. Nature 2005, vol. 437, p. 276-380.*
Downs. "Prospects for Nucleic Acid Biosensors." 1991.
Kunz. "Totally Integrated Optical Measuring Sensors." 1991.
Eggers, et al. "A Microchip for Quantitative Detection of Molecules Utilizing Luminescent and Radioisotope Reporter Groups." 1994.
Lamture et al. "Direct Detection of Nucleic Acid Hybridization on the Surface of a Charge Coupled Device," 1994.
Eggers et al. "A Review of Microfabricated Devices for Gene-Based Diagnostics." 1995.

(Continued)

*Primary Examiner* — John S. Brusca
*Assistant Examiner* — Olivia M Wise
(74) *Attorney, Agent, or Firm* — Illumina, Inc.

(57) ABSTRACT

Method of analyzing signal data from a biosensor including a detection device having an array of light detectors. The method includes obtaining signal data from the light detectors. The signal data includes light scores that are based on an amount of light detected by the light detectors during a plurality of imaging events. The method also includes analyzing the light scores from a group of light detectors for each of the plurality of imaging events. The method also includes determining respective crosstalk functions of the light detectors in the group. Each of the crosstalk functions for a corresponding light detector is based on the amount of light detected by other light detectors in the group. The method also includes analyzing the signal data for each of the imaging events using the crosstalk functions to determine characteristics of the analytes-of-interest.

20 Claims, 17 Drawing Sheets

(56) References Cited

U.S. PATENT DOCUMENTS

| | | |
|---|---|---|
| 6,921,908 B2 | 7/2005 | Reel |
| 6,940,590 B2 | 9/2005 | Colvin |
| 6,946,286 B2 | 9/2005 | Howard |
| 6,975,251 B2 | 12/2005 | Pavicic |
| 6,982,519 B2 | 1/2006 | Guillorn |
| 6,995,386 B2 | 2/2006 | Emoto |
| 7,005,264 B2 | 2/2006 | Su |
| 7,013,033 B2 | 3/2006 | Arena |
| 7,075,104 B2 | 7/2006 | Faris |
| 7,145,645 B2 | 12/2006 | Blumenfeld |
| 7,163,822 B2 | 1/2007 | Yazawa |
| 7,170,605 B2 | 1/2007 | Cromwell |
| 7,179,654 B2 | 2/2007 | Verdonk |
| 7,190,445 B2 | 3/2007 | Colvin |
| 7,221,455 B2 | 5/2007 | Chediak |
| 7,244,559 B2 * | 7/2007 | Rothberg ............. B01L 3/5027 435/5 |
| 7,258,731 B2 | 8/2007 | D'Urso |
| 7,280,201 B2 | 10/2007 | Helbing |
| 7,308,292 B2 | 12/2007 | Colvin |
| 7,349,093 B2 | 3/2008 | Tabata |
| 7,371,538 B2 | 5/2008 | Simpson |
| 7,371,564 B2 | 5/2008 | Kwon |
| 7,413,852 B2 | 8/2008 | Balch |
| 7,416,915 B2 | 8/2008 | Kasano |
| 7,433,552 B2 | 10/2008 | Kiesel |
| 7,454,296 B2 | 11/2008 | Wang |
| 7,463,353 B2 | 12/2008 | Yershov |
| 7,466,409 B2 | 12/2008 | Scherer |
| 7,489,401 B2 | 2/2009 | Kamei |
| 7,502,123 B2 | 3/2009 | Schmidt |
| 7,524,459 B2 | 4/2009 | Adams |
| 7,541,176 B2 | 6/2009 | Raynor |
| 7,585,664 B2 | 9/2009 | Chan |
| 7,595,883 B1 | 9/2009 | El Gamal |
| 7,604,981 B1 | 10/2009 | Harris |
| 7,609,379 B2 | 10/2009 | Canioni |
| 7,629,591 B2 | 12/2009 | Nelson |
| 7,638,182 B2 | 12/2009 | D'Urso |
| 7,738,086 B2 | 6/2010 | Shepard |
| 7,750,354 B2 | 7/2010 | Kasano |
| 7,767,441 B2 | 8/2010 | Chiou |
| 7,782,237 B2 | 8/2010 | Ronaghi |
| 7,811,810 B2 | 10/2010 | Chiou |
| 7,812,324 B2 | 10/2010 | Connally |
| 7,839,450 B2 | 11/2010 | Hing |
| 2003/0108867 A1 * | 6/2003 | Chee .................... C12Q 1/6869 435/6.11 |
| 2007/0146704 A1 | 6/2007 | Schmidt |
| 2007/0281288 A1 | 12/2007 | Belkin |
| 2008/0039339 A1 | 2/2008 | Hassibi |
| 2008/0081769 A1 | 4/2008 | Hassibi |
| 2008/0176757 A1 | 7/2008 | Hassibi |
| 2008/0203452 A1 | 8/2008 | Moon |
| 2009/0075838 A1 | 3/2009 | El Gamal |
| 2009/0197326 A1 | 8/2009 | El Gamal |
| 2009/0258413 A1 | 10/2009 | Moriwaki |
| 2009/0279093 A1 | 11/2009 | Van Herpen |
| 2009/0284746 A1 | 11/2009 | Klunder |
| 2009/0325164 A1 | 12/2009 | Vossenaar |
| 2010/0015611 A1 | 1/2010 | Webster |
| 2010/0055666 A1 | 3/2010 | Wimberger-Friedl |
| 2010/0065726 A1 | 3/2010 | Zhong |
| 2010/0108865 A1 | 5/2010 | Cho |
| 2010/0111762 A1 | 5/2010 | Cho |
| 2010/0112342 A1 | 5/2010 | Cho |
| 2010/0122904 A1 | 5/2010 | Hassibi |
| 2010/0200781 A1 | 8/2010 | Khorasani |
| 2010/0204064 A1 | 8/2010 | Cho |
| 2010/0210475 A1 | 8/2010 | Lee |
| 2010/0230610 A1 | 9/2010 | Van Der Zaag |
| 2012/0021525 A1 | 1/2012 | Fehr |

OTHER PUBLICATIONS

Burns, et al. "Microfabricated Structures for Integrated DNA Analysis." May 1996.

Eggers et al. "A Versatile Biochip for Gene-Based Diagnostics." 1996.

Kunz, "Miniature integrated Optical Modules for Chemical and Biochemical Sensing." 1997.

Schmaizing, et al. "DNA Typing in Thirty Seconds with a Microfabricated Device," Sep. 1997.

Caillat, et al. "SA 17.1: Active CMOS Biochips: An Electro-Addressed DNA Probe," 1998.

Mastrangelo, et al. "Microfabricated Devices for Genetic Diagnostics." Aug. 1998.

Caillat, et al, "Biochips on CMOS: An Active Matrix Address Array for DNA Analysis." 1999.

Vo Dinh et al. "DNA Biochip Using a Photofransistor Integrated Circuit." Jan. 15, 1999.

* cited by examiner

|   | 1  | 2  | 3  |
|---|----|----|----|
| E | 15 | 80 | 15 |
| F | 15 | 85 | 15 |
| G | 5  | 15 | 75 |

1st Imaging Event

|   | 1  | 2  | 3  |
|---|----|----|----|
| E | 20 | 80 | 80 |
| F | 85 | 60 | 25 |
| G | 90 | 80 | 80 |

2nd Imaging Event

|   | 1   | 2   | 3  |
|---|-----|-----|----|
| E | 85  | 30  | 15 |
| F | 100 | 105 | 90 |
| G | 85  | 40  | 85 |

3rd Imaging Event

BIOSENSORS FOR BIOLOGICAL OR CHEMICAL ANALYSIS AND SYSTEMS AND METHODS FOR SAME

CROSS-REFERENCE TO RELATED APPLICATION

The present application is a divisional of U.S. application Ser. No. 13/833,619 ("the '619 Application"), filed on Mar. 15, 2013, which claims the benefit of U.S. Provisional Application No. 61/625,051 ("the '051 Application"), which was filed on Apr. 16, 2012. Each of the '619 and the '051 Applications is incorporated herein by reference in its entirety.

BACKGROUND OF THE INVENTION

Embodiments of the present invention relate generally to biological or chemical analysis and more particularly to systems and methods using detection devices for biological or chemical analysis.

Various protocols in biological or chemical research involve performing a large number of controlled reactions on local support surfaces or within predefined reaction chambers. The desired reactions may then be observed or detected and subsequent analysis may help identify or reveal properties of chemicals involved in the reaction. For example, in some multiplex assays, an unknown analyte having an identifiable label (e.g., fluorescent label) may be exposed to thousands of known probes under controlled conditions. Each known probe may be deposited into a corresponding well of a microplate. Observing any chemical reactions that occur between the known probes and the unknown analyte within the wells may help identify or reveal properties of the analyte. Other examples of such protocols include known DNA sequencing processes, such as sequencing-by-synthesis (SBS) or cyclic-array sequencing.

In some conventional fluorescent-detection protocols, an optical system is used to direct an excitation light onto fluorescently-labeled analytes and to also detect the fluorescent signals that may emit from the analytes. However, such optical systems can be relatively expensive and require a larger benchtop footprint. For example, the optical system may include an arrangement of lenses, filters, and light sources. In other proposed detection systems, the controlled reactions occur immediately over a solid-state imager (e.g., charged-coupled device (CCD) or a complementary metal-oxide-semiconductor (CMOS) detector) that does not require a large optical assembly to detect the fluorescent emissions.

However, the proposed solid-state imaging systems may have some limitations. For example, it may be challenging to distinguish the fluorescent emissions from the excitation light when the excitation light is also directed toward the light detectors of the solid-state imager. In addition, fluidicly delivering reagents to analytes that are located on an electronic device and in a controlled manner may present additional challenges. As another example, fluorescent emissions are substantially isotropic. As the density of the analytes on the solid-state imager increases, it becomes increasingly challenging to manage or account for unwanted light emissions from adjacent analytes (e.g., crosstalk).

BRIEF DESCRIPTION OF THE INVENTION

In accordance with one embodiment, a biosensor is provided that includes a flow cell mounted to a detection device. The detection device has a detector surface with a plurality of reaction sites. The detection device includes a filter layer that is configured to at least one of (a) filter unwanted light signals, such as light signals from excitation light; (b) direct emission signals from a designated reaction site toward one or more detectors that are configured to detect the emission signals from the designated reaction site; or (c) block or prevent detection of emission signals from adjacent reaction sites.

In another embodiment, a biosensor is provided that includes a flow cell and a detection device having a plurality of stacked layers and a detector surface configured to support reaction sites. The stacked layers include a filter layer and a solid-state imager coupled to the filter layer. The filter layer includes filter walls and a light-absorbing material that is deposited between adjacent filter walls. The light-absorbing material configured to prevent transmission of excitation signals and permit transmission of fluorescent signals. Adjacent filter walls define a detection path therebetween through the corresponding light-absorbing material toward the solid-state imager. The filter walls are configured to reflect the fluorescent signals. The flow cell is mounted to the detector surface thereby defining a flow channel between at least one surface of the flow cell (e.g. an exterior surface of the flow cell) and the detection device. The surface of the flow cell can includes a material that permits transmission of the excitation signals. Thus, the surface can function to retain fluid in the flow channel while passing excitation light to the fluid.

In another embodiment, a method of analyzing fluorescent signals detected from an array of reaction sites having corresponding analytes-of-interest. The method includes performing first and second imaging events using a detection device (e.g., CMOS imager) having an array of light detectors in which (a) fluorescent signals emitting from a first set of reaction sites are captured during the first imaging event and (b) fluorescent signals emitting from a different second set of reaction sites are captured during the second imaging event. For each of the first and second imaging events, the light detectors have a light score that corresponds to an amount of fluorescence detected during the corresponding imaging event. The method can also include identifying an amount of crosstalk that is detected by a first light detector when an adjacent second light detector detects a positive binding event. The method can also include analyzing the light scores from the first and second imaging events to determine information about the analytes-of-interest, wherein the analyzing includes accounting for the crosstalk detected by light detectors.

In yet another embodiment, a method of detecting fluorescent signals from an array of reaction sites that are distributed along a detector surface of a detection device is provided. The method includes providing the detection device including the detector surface and a solid-state imager having light detectors. The detection device also includes filter walls that extend between and define detection paths between the detector surface and associated light detectors of the solid-state imager. The detection paths include first and second detection paths, and the light detectors include first and second light detectors that detect light signals propagating along the first and second detection paths, respectively. The first and second detection paths are adjacent to each other and the first and second light detectors are adjacent to each other. The method can also include, during a first imaging event, detecting a positive portion of fluorescent signals from a first reaction site on the detector surface with the first light detector. The positive portion indicates that a desired reaction has occurred at the first reaction site. The method can also include, during the first imaging event, detecting a crosstalk portion of the fluorescent signals from the first reaction site with the second light detector, wherein the crosstalk portion is less than the positive portion. The method can also include, during a second imaging event, detecting a positive portion of fluorescent signals from a second reaction site on the detector surface with the second light detector. The positive portion indicates that a desired reaction has occurred at the second reaction site. The method can also include analyzing the detected fluorescent signals to determine information about analytes-of-interest at the first and second reaction sites. The analyzing optionally includes accounting for the crosstalk portion.

In another embodiment, a method of analyzing signal data from a biosensor including a detection device is provided. The detection device includes an array of light detectors. Each of the light detectors is associated with at least one reaction site. The reaction sites include analytes-of-interest. The method includes obtaining the signal data from the light detectors. The signal data includes light scores that are based on an amount of light detected by the light detectors during a plurality of imaging events. The method also includes analyzing the light scores from a set of light detectors for each of the plurality of the imaging events. The method also includes determining respective crosstalk functions of the light detectors in the set in which each of the crosstalk functions is based on an amount of light detected by other light detectors in the set. The method also includes analyzing the signal data for each of the imaging events using the crosstalk functions to determine characteristics of the analytes-of-interest.

DETAILED DESCRIPTION OF THE INVENTION

Figure 1:
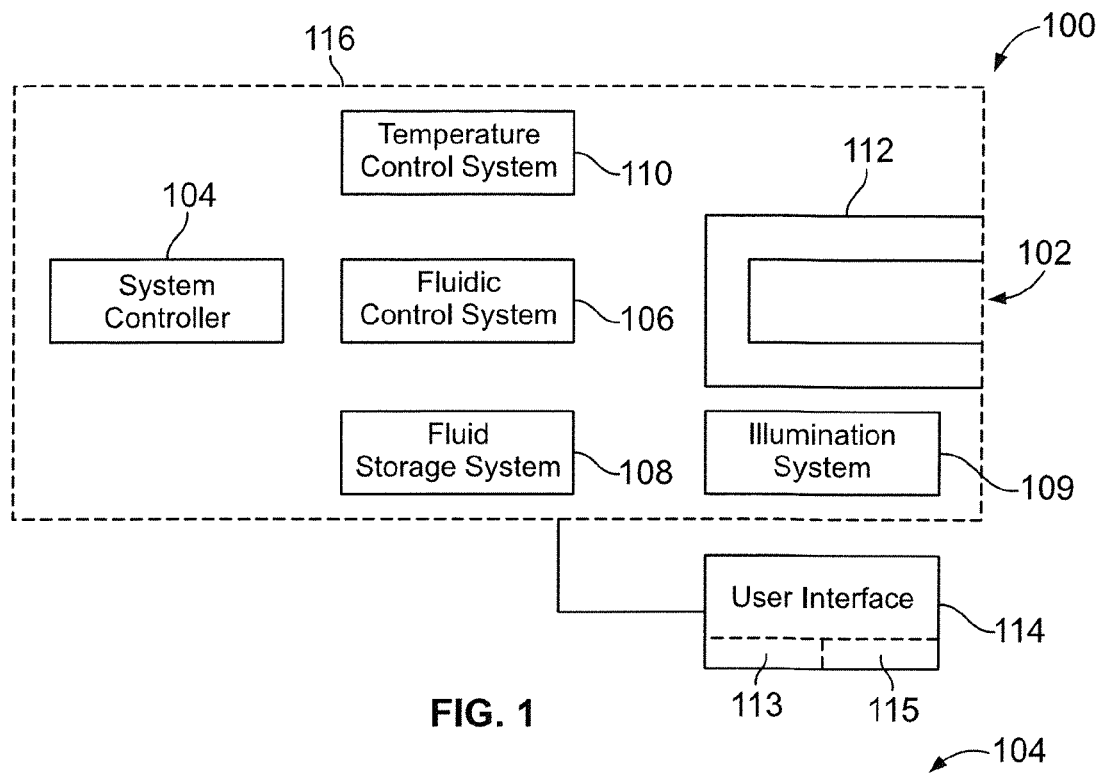
FIG. 1 is a block diagram of an exemplary system for biological or chemical analysis formed in accordance with one embodiment.

Embodiments described herein may be used in various biological or chemical processes and systems for academic or commercial analysis. More specifically, embodiments described herein may be used in various processes and systems where it is desired to detect an event, property, quality, or characteristic that is indicative of a desired reaction. For example, embodiments described herein include cartridges, biosensors, and their components as well as bioassay systems that operate with cartridges and biosensors. In particular embodiments, the cartridges and biosensors include a flow cell and one or more light detectors that are coupled together in a substantially unitary structure.

The bioassay systems may be configured to perform a plurality of desired reactions that may be detected individually or collectively. The biosensors and bioassay systems may be configured to perform numerous cycles in which the plurality of desired reactions occurs in parallel. For example, the bioassay systems may be used to sequence a dense array of DNA features through iterative cycles of enzymatic manipulation and image acquisition. As such, the cartridges and biosensors may include one or more microfluidic channels that deliver reagents or other reaction components to a reaction site. In some embodiments, the reaction sites are randomly distributed across a substantially planer surface. For example, the reaction sites may have an uneven distribution in which some reaction sites are located closer to each other than other reaction sites. In other embodiments, the reaction sites are patterned across a substantially planer surface in a predetermined manner. Each of the reaction sites may be associated with one or more light detectors that detect light from the associated reaction site. Yet in other embodiments, the reaction sites are located in reaction chambers that compartmentalize the desired reactions therein.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements whether or not they have that property.

As used herein, a "desired reaction" includes a change in at least one of a chemical, electrical, physical, or optical property (or quality) of an analyte-of-interest. In particular embodiments, the desired reaction is a positive binding event (e.g., incorporation of a fluorescently labeled biomolecule with the analyte-of-interest). More generally, the desired reaction may be a chemical transformation, chemical change, or chemical interaction. The desired reaction may also be a change in electrical properties. For example, the desired reaction may be a change in ion concentration within a solution. Exemplary reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; bioluminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The desired reaction can also be addition or elimination of a proton, for example, detectable as a change in pH of a surrounding solution or environment. An additional desired reaction can be detecting the flow of ions across a membrane (e.g., natural or synthetic bilayer membrane), for example as ions flow through a membrane the current is disrupted and the disruption can be detected.

In particular embodiments, the desired reaction includes the incorporation of a fluorescently-labeled molecule to an analyte. The analyte may be an oligonucleotide and the fluorescently-labeled molecule may be a nucleotide. The desired reaction may be detected when an excitation light is directed toward the oligonucleotide having the labeled nucleotide, and the fluorophore emits a detectable fluorescent signal. In alternative embodiments, the detected fluorescence is a result of chemiluminescence or bioluminescence. A desired reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction component" or "reactant" includes any substance that may be used to obtain a desired reaction. For example, reaction components include reagents, enzymes, samples, other biomolecules, and buffer solutions. The reaction components are typically delivered to a reaction site in a solution and/or immobilized at a reaction site. The reaction components may interact directly or indirectly with another substance, such as the analyte-of-interest.

As used herein, the term "reaction site" is a localized region where a desired reaction may occur. A reaction site may include support surfaces of a substrate where a substance may be immobilized thereon. For example, a reaction site may include a substantially planar surface in a channel of a flow cell that has a colony of nucleic acids thereon. Typically, but not always, the nucleic acids in the colony have the same sequence, being for example, clonal copies of a single stranded or double stranded template. However, in some embodiments a reaction site may contain only a single nucleic acid molecule, for example, in a single stranded or double stranded form. Furthermore, a plurality of reaction sites may be randomly distributed along the support surface or arranged in a predetermined manner (e.g., side-by-side in a matrix, such as in microarrays). A reaction site can also include a reaction chamber that at least partially defines a spatial region or volume configured to compartmentalize the desired reaction. As used herein, the term "reaction chamber" includes a spatial region that is in fluid communication with a flow channel. The reaction chamber may be at least partially separated from the surrounding environment or other spatial regions. For example, a plurality of reaction chambers may be separated from each other by shared walls. As a more specific example, the reaction chamber may include a cavity defined by interior surfaces of a well and have an opening or aperture so that the cavity may be in fluid communication with a flow channel. Biosensors including such reaction chambers are described in greater detail in international application no. PCT/US2011/057111, filed on Oct. 20, 2011, which is incorporated herein by reference in its entirety.

In some embodiments, the reaction chambers are sized and shaped relative to solids (including semi-solids) so that the solids may be inserted, fully or partially, therein. For example, the reaction chamber may be sized and shaped to accommodate only one capture bead. The capture bead may have clonally amplified DNA or other substances thereon. Alternatively, the reaction chamber may be sized and shaped to receive an approximate number of beads or solid substrates. As another example, the reaction chambers may also be filled with a porous gel or substance that is configured to control diffusion or filter fluids that may flow into the reaction chamber.

In some embodiments, light detectors (e.g., photodiodes) are associated with corresponding reaction sites. A light detector that is associated with a reaction site is configured to detect light emissions from the associated reaction site when a desired reaction has occurred at the associated reaction site. In some cases, a plurality of light detectors (e.g. several pixels of a camera device) may be associated with a single reaction site. In other cases, a single light detector (e.g. a single pixel) may be associated with a single reaction site or with a group of reaction sites. The light detector, the reaction site, and other features of the biosensor may be configured so that at least some of the light is directly detected by the light detector without being reflected.

As used herein, the term "adjacent" when used with respect to two reaction sites means no other reaction site is located between the two reaction sites. The term "adjacent" may have a similar meaning when used with respect to adjacent detection paths and adjacent light detectors (e.g., adjacent light detectors have no other light detector therebetween). In some cases, a reaction site may not be adjacent to another reaction site, but may still be within an immediate vicinity of the other reaction site. A first reaction site may be in the immediate vicinity of a second reaction site when fluorescent emission signals from the first reaction site are detected by the light detector associated with the second reaction site. More specifically, a first reaction site may be in the immediate vicinity of a second reaction site when the light detector associated with the second reaction site detects, for example crosstalk from the first reaction site. Adjacent reaction sites can be contiguous such that they abut each other or the adjacent sites can be non-contiguous having an intervening space between.

As used herein, a "substance" includes items or solids, such as capture beads, as well as biological or chemical substances. As used herein, a "biological or chemical substance" includes biomolecules, samples-of-interest, analytes-of-interest, and other chemical compound(s). A biological or chemical substance may be used to detect, identify, or analyze other chemical compound(s), or function as intermediaries to study or analyze other chemical compound(s). In particular embodiments, the biological or chemical substances include a biomolecule. As used herein, a "biomolecule" includes at least one of a biopolymer, nucleoside, nucleic acid, polynucleotide, oligonucleotide, protein, enzyme, polypeptide, antibody, antigen, ligand, receptor, polysaccharide, carbohydrate, polyphosphate, cell, tissue, organism, or fragment thereof or any other biologically active chemical compound(s) such as analogs or mimetics of the aforementioned species.

In a further example, a biological or chemical substance or a biomolecule includes an enzyme or reagent used in a coupled reaction to detect the product of another reaction such as an enzyme or reagent used to detect pyrophosphate in a pyrosequencing reaction. Enzymes and reagents useful for pyrophosphate detection are described, for example, in U.S. Patent Publication No. 2005/0244870 A1, which is incorporated herein in its entirety.

Biomolecules, samples, and biological or chemical substances may be naturally occurring or synthetic and may be suspended in a solution or mixture within a spatial region. Biomolecules, samples, and biological or chemical substances may also be bound to a solid phase or gel material. Biomolecules, samples, and biological or chemical substances may also include a pharmaceutical composition. In some cases, biomolecules, samples, and biological or chemical substances of interest may be referred to as targets, probes, or analytes.

As used herein, a "biosensor" includes a structure having a plurality of reaction sites. A biosensor may include a solid-state imaging device (e.g., CCD or CMOS imager) and, optionally, a flow cell mounted thereto. The flow cell may include at least one flow channel that is in fluid communication with the reaction sites. As one specific example, the biosensor is configured to fluidicly and electrically couple to a bioassay system. The bioassay system may deliver reactants to the reaction sites according to a predetermined protocol (e.g., sequencing-by-synthesis) and perform a plurality of imaging events. For example, the bioassay system may direct solutions to flow along the reaction sites. At least one of the solutions may include four types of nucleotides having the same or different fluorescent labels. The nucleotides may bind to corresponding oligonucleotides located at the reaction sites. The bioassay system may then illuminate the reaction sites using an excitation light source (e.g., solid-state light sources, such as light-emitting diodes or LEDs). The excitation light may have a predetermined wavelength or wavelengths, including a range of wavelengths. The excited fluorescent labels provide emission signals that may be detected by the light detectors.

In alternative embodiments, the biosensor may include electrodes or other types of sensors configured to detect other identifiable properties. For example, the sensors may be configured to detect a change in ion concentration. In another example, the sensors may be configured to detect the ion current flow across a membrane As used herein, a "cartridge" includes a structure that is configured to hold a biosensor. In some embodiments, the cartridge may include additional features, such as the light source (e.g., LEDs) that are configured to provide excitation light to the reactions sites of the biosensor. The cartridge may also include a fluidic storage system (e.g., storage for reagents, sample, and buffer) and a fluidic control system (e.g., pumps, valves, and the like) for fluidically transporting reaction components, sample, and the like to the reaction sites. For example, after the biosensor is prepared or manufactured, the biosensor may be coupled to a housing or container of the cartridge. In some embodiments, the biosensors and the cartridges may be self-contained, disposable units. However, other embodiments may include an assembly with removable parts that allow a user to access an interior of the biosensor or cartridge for maintenance or replacement of components or samples. The biosensor and the cartridge may be removably coupled or engaged to larger bioassay systems, such as a sequencing system, that conducts controlled reactions therein.

As used herein, when the terms "removably" and "coupled" (or "engaged") are used together to describe a relationship between the biosensor (or cartridge) and a system receptacle or interface of a bioassay system, the term is intended to mean that a connection between the biosensor (or cartridge) and the system receptacle is readily separable without destroying or damaging the system receptacle and/ or the biosensor (or cartridge). Components are readily separable when the components may be separated from each other without undue effort or a significant amount of time spent in separating the components. For example, the biosensor (or cartridge) may be removably coupled or engaged to the system receptacle in an electrical manner such that the mating contacts of the bioassay system are not destroyed or damaged. The biosensor (or cartridge) may also be removably coupled or engaged to the system receptacle in a mechanical manner such that the features that hold the biosensor (or cartridge) are not destroyed or damaged. The biosensor (or cartridge) may also be removably coupled or engaged to the system receptacle in a fluidic manner such that the ports of the system receptacle are not destroyed or damaged. The system receptacle or a component is not considered to be destroyed or damaged if, for example, only a simple adjustment to the component (e.g., realignment) or a simple replacement (e.g., replacing a nozzle) is required.

As used herein, the term "fluid communication" or "fluidicly coupled" refers to two spatial regions being connected together such that a liquid or gas may flow between the two spatial regions. For example, a microfluidic channel may be in fluid communication with a reaction chamber such that a fluid may flow freely into the reaction chamber from the microfluidic channel. The terms "in fluid communication" or "fluidicly coupled" allow for two spatial regions being in fluid communication through one or more valves, restrictors, or other fluidic components that are configured to control or regulate a flow of fluid through a system.

As used herein, the term "immobilized," when used with respect to a biomolecule or biological or chemical substance, includes substantially attaching the biomolecule or biological or chemical substance at a molecular level to a surface. For example, a biomolecule or biological or chemical substance may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to a surface of a substrate material may be based upon the properties of the substrate surface, the liquid medium carrying the biomolecule or biological or chemical substance, and the properties of the biomolecules or biological or chemical substances themselves. In some cases, a substrate surface may be functionalized (e.g., chemically or physically modified) to facilitate immobilizing the biomolecules (or biological or chemical substances) to the substrate surface. The substrate surface may be first modified to have functional groups bound to the surface. The functional groups may then bind to biomolecules or biological or chemical substances to immobilize them thereon. A substance can be immobilized to a surface via a gel, for example, as described in US Patent Publ. No. US 2011/0059865 A1, which is incorporated herein by reference.

In some embodiments, nucleic acids can be attached to a surface and amplified using bridge amplification. Useful bridge amplification methods are described, for example, in U.S. Pat. No. 5,641,658; WO 07/010,251, U.S. Pat. No. 6,090,592; U.S. Patent Publ. No. 2002/0055100 A1; U.S. Pat. No. 7,115,400; U.S. Patent Publ. No. 2004/0096853 A1; U.S. Patent Publ. No. 2004/0002090 A1; U.S. Patent Publ. No. 2007/0128624 A1; and U.S. Patent Publ. No. 2008/0009420 A1, each of which is incorporated herein in its entirety. Another useful method for amplifying nucleic acids on a surface is rolling circle amplification (RCA), for example, using methods set forth in further detail below. In some embodiments, the nucleic acids can be attached to a surface and amplified using one or more primer pairs. For example, one of the primers can be in solution and the other primer can be immobilized on the surface (e.g., 5'-attached). By way of example, a nucleic acid molecule can hybridize to one of the primers on the surface followed by extension of the immobilized primer to produce a first copy of the nucleic acid. The primer in solution then hybridizes to the first copy of the nucleic acid which can be extended using the first copy of the nucleic acid as a template. Optionally, after the first copy of the nucleic acid is produced, the original nucleic acid molecule can hybridize to a second immobilized primer on the surface and can be extended at the same time or after the primer in solution is extended. In any embodiment, repeated rounds of extension (e.g., amplification) using the immobilized primer and primer in solution provide multiple copies of the nucleic acid.

In particular embodiments, the assay protocols executed by the systems and methods described herein include the use of natural nucleotides and also enzymes that are configured to interact with the natural nucleotides. Natural nucleotides include, for example, ribonucleotides or deoxyribonucleotides. Natural nucleotides can be in the mono-, di-, or tri-phosphate form and can have a base selected from adenine (A), Thymine (T), uracil (U), guanine (G) or cytosine (C). It will be understood however that non-natural nucleotides, modified nucleotides or analogs of the aforementioned nucleotides can be used. Some examples of useful non-natural nucleotides are set forth below in regard to reversible terminator-based sequencing by synthesis methods.

In embodiments that include reaction chambers, items or solid substances (including semi-solid substances) may be disposed within the reaction chambers. When disposed, the item or solid may be physically held or immobilized within the reaction chamber through an interference fit, adhesion, or entrapment. Exemplary items or solids that may be disposed within the reaction chambers include polymer beads, pellets, agarose gel, powders, quantum dots, or other solids that may be compressed and/or held within the reaction chamber. In particular embodiments, a nucleic acid superstructure, such as a DNA ball, can be disposed in or at a reaction chamber, for example, by attachment to an interior surface of the reaction chamber or by residence in a liquid within the reaction chamber. A DNA ball or other nucleic acid superstructure can be preformed and then disposed in or at the reaction chamber. Alternatively, a DNA ball can be synthesized in situ at the reaction chamber. A DNA ball can be synthesized by rolling circle amplification to produce a concatamer of a particular nucleic acid sequence and the concatamer can be treated with conditions that form a relatively compact ball. DNA balls and methods for their synthesis are described, for example in, U.S. Patent Publ. Nos. 2008/0242560 A1 or 2008/0234136 A1, each of which is incorporated herein in its entirety. A substance that is held or disposed in a reaction chamber can be in a solid, liquid, or gaseous state.

FIG. 1 is a block diagram of an exemplary bioassay system 100 for biological or chemical analysis formed in accordance with one embodiment. The term "bioassay" is not intended to be limiting as the bioassay system 100 may operate to obtain any information or data that relates to at least one of a biological or chemical substance. In some embodiments, the bioassay system 100 is a workstation that may be similar to a bench-top device or desktop computer. For example, a majority (or all) of the systems and components for conducting the desired reactions can be within a common housing 116.

In particular embodiments, the bioassay system 100 is a nucleic acid sequencing system (or sequencer) configured for various applications, including but not limited to de novo sequencing, resequencing of whole genomes or target genomic regions, and metagenomics. The sequencer may also be used for DNA or RNA analysis. In some embodiments, the bioassay system 100 may also be configured to generate reaction sites in a biosensor. For example, the bioassay system 100 may be configured to receive a sample and generate surface attached clusters of clonally amplified nucleic acids derived from the sample. Each cluster may constitute or be part of a reaction site in the biosensor.

The exemplary bioassay system 100 may include a system receptacle or interface 112 that is configured to interact with a biosensor 102 to perform desired reactions within the biosensor 102. In the following description with respect to FIG. 1, the biosensor 102 is loaded into the system receptacle 112. However, it is understood that a cartridge that includes the biosensor 102 may be inserted into the system receptacle 112 and in some states the cartridge can be removed temporarily or permanently. As described above, the cartridge may include, among other things, fluidic control and fluidic storage components.

In particular embodiments, the bioassay system 100 is configured to perform a large number of parallel reactions within the biosensor 102. The biosensor 102 includes one or more reaction sites where desired reactions can occur. The reaction sites may be, for example, immobilized to a solid surface of the biosensor or immobilized to beads (or other movable substrates) that are located within corresponding reaction chambers of the biosensor. The reaction sites can include, for example, clusters of clonally amplified nucleic acids. The biosensor 102 may include a solid-state imaging device (e.g., CCD or CMOS imager) and a flow cell mounted thereto. The flow cell may include one or more flow channels that receive a solution from the bioassay system 100 and direct the solution toward the reaction sites. Optionally, the biosensor 102 can be configured to engage a thermal element for transferring thermal energy into or out of the flow channel.

The bioassay system 100 may include various components, assemblies, and systems (or sub-systems) that interact with each other to perform a predetermined method or assay protocol for biological or chemical analysis. For example, the bioassay system 100 includes a system controller 104 that may communicate with the various components, assemblies, and sub-systems of the bioassay system 100 and also the biosensor 102. For example, in addition to the system receptacle 112, the bioassay system 100 may also include a fluidic control system 106 to control the flow of fluid throughout a fluid network of the bioassay system 100 and the biosensor 102; a fluid storage system 108 that is configured to hold all fluids (e.g., gas or liquids) that may be used by the bioassay system; a temperature control system 110 that may regulate the temperature of the fluid in the fluid network, the fluid storage system 108, and/or the biosensor 102; and an illumination system 111 that is configured to illuminate the biosensor 102. As described above, if a cartridge having the biosensor 102 is loaded into the system receptacle 112, the cartridge may also include fluidic control and fluidic storage components.

Also shown, the bioassay system 100 may include a user interface 114 that interacts with the user. For example, the user interface 114 may include a display 113 to display or request information from a user and a user input device 115 to receive user inputs. In some embodiments, the display 113 and the user input device 115 are the same device. For example, the user interface 114 may include a touch-sensitive display configured to detect the presence of an individual's touch and also identify a location of the touch on the display. However, other user input devices 115 may be used, such as a mouse, touchpad, keyboard, keypad, handheld scanner, voice-recognition system, motion-recognition system, and the like. As will be discussed in greater detail below, the bioassay system 100 may communicate with various components, including the biosensor 102 (e.g. in the form of a cartridge), to perform the desired reactions. The bioassay system 100 may also be configured to analyze data obtained from the biosensor to provide a user with desired information.

The system controller 104 may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. The above examples are exemplary only, and are thus not intended to limit in any way the definition and/or meaning of the term system controller. In the exemplary embodiment, the system controller 104 executes a set of instructions that are stored in one or more storage elements, memories, or modules in order to at least one of obtain and analyze detection data. Storage elements may be in the form of information sources or physical memory elements within the bioassay system 100.

The set of instructions may include various commands that instruct the bioassay system 100 or biosensor 102 to perform specific operations such as the methods and processes of the various embodiments described herein. The set of instructions may be in the form of a software program, which may form part of a tangible, non-transitory computer readable medium or media. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the bioassay system 100, processed in response to user inputs, or processed in response to a request made by another processing machine (e.g., a remote request through a communication link).

The system controller 104 may be connected to the biosensor 102 and the other components of the bioassay system 100 via communication links. The system controller 104 may also be communicatively connected to off-site systems or servers. The communication links may be hard-wired or wireless. The system controller 104 may receive user inputs or commands, from the user interface 114 and the user input device 115.

The fluidic control system 106 includes a fluid network and is configured to direct and regulate the flow of one or more fluids through the fluid network. The fluid network may be in fluid communication with the biosensor 102 and the fluid storage system 108. For example, select fluids may be drawn from the fluid storage system 108 and directed to the biosensor 102 in a controlled manner, or the fluids may be drawn from the biosensor 102 and directed toward, for example, a waste reservoir in the fluid storage system 108. Although not shown, the fluidic control system 106 may include flow sensors that detect a flow rate or pressure of the fluids within the fluid network. The sensors may communicate with the system controller 104.

The temperature control system 110 is configured to regulate the temperature of fluids at different regions of the fluid network, the fluid storage system 108, and/or the biosensor 102. For example, the temperature control system 110 may include a thermocycler that interfaces with the biosensor 102 and controls the temperature of the fluid that flows along the reaction sites in the biosensor 102. The temperature control system 110 may also regulate the temperature of solid elements or components of the bioassay system 100 or the biosensor 102. Although not shown, the temperature control system 110 may include sensors to detect the temperature of the fluid or other components. The sensors may communicate with the system controller 104.

The fluid storage system 108 is in fluid communication with the biosensor 102 and may store various reaction components or reactants that are used to conduct the desired reactions therein. The fluid storage system 108 may also store fluids for washing or cleaning the fluid network and biosensor 102 and for diluting the reactants. For example, the fluid storage system 108 may include various reservoirs to store samples, reagents, enzymes, other biomolecules, buffer solutions, aqueous, and non-polar solutions, and the like. Furthermore, the fluid storage system 108 may also include waste reservoirs for receiving waste products from the biosensor 102. In embodiments that include a cartridge, the cartridge may include one or more of a fluid storage system, fluidic control system or temperature control system. Accordingly, one or more of the components set forth herein as relating to those systems can be contained within a cartridge housing. For example, a cartridge can have various reservoirs to store samples, reagents, enzymes, other biomolecules, buffer solutions, aqueous, and non-polar solutions, waste, and the like. As such, one or more of a fluid storage system, fluidic control system or temperature control system can be removably engaged with a bioassay system via a cartridge or other biosensor.

The illumination system 111 may include a light source (e.g., one or more LEDs) and a plurality of optical components to illuminate the biosensor. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In embodiments that use an illumination system, the illumination system 111 may be configured to direct an excitation light to reaction sites. As one example, fluorophores may be excited by green wavelengths of light, as such the wavelength of the excitation light may be approximately 532 nm.

The system receptacle or interface 112 is configured to engage the biosensor 102 in at least one of a mechanical, electrical, and fluidic manner. The system receptacle 112 may hold the biosensor 102 in a desired orientation to facilitate the flow of fluid through the biosensor 102. The system receptacle 112 may also include electrical contacts that are configured to engage the biosensor 102 so that the bioassay system 100 may communicate with the biosensor 102 and/or provide power to the biosensor 102. Furthermore, the system receptacle 112 may include fluidic ports (e.g., nozzles) that are configured to engage the biosensor 102. In some embodiments, the biosensor 102 is removably coupled to the system receptacle 112 in a mechanical manner, in an electrical manner, and also in a fluidic manner.

In addition, the bioassay system 100 may communicate remotely with other systems or networks or with other bioassay systems 100. Detection data obtained by the bioassay system(s) 100 may be stored in a remote database.

Figure 2:
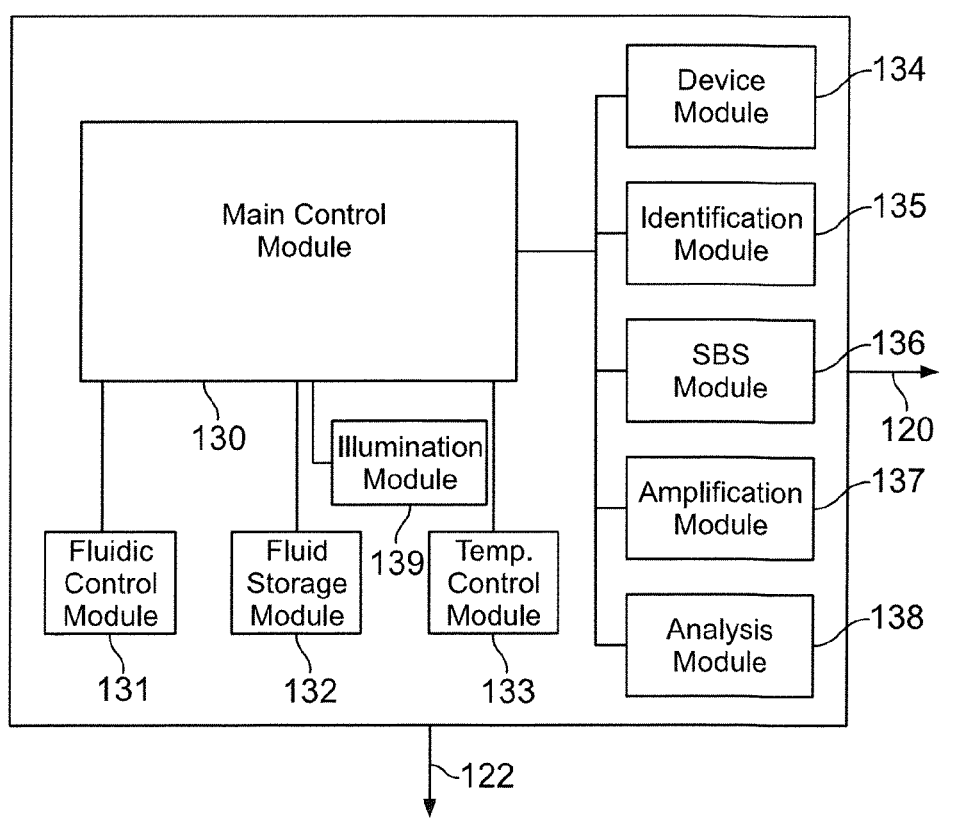
FIG. 2 is a block diagram of an exemplary system controller that may be used in the system of FIG. 1.

FIG. 2 is a block diagram of the system controller 104 in the exemplary embodiment. In one embodiment, the system controller 104 includes one or more processors or modules that can communicate with one another. Each of the processors or modules may include an algorithm (e.g., instructions stored on a tangible and/or non-transitory computer readable storage medium) or sub-algorithms to perform particular processes. The system controller 104 is illustrated conceptually as a collection of modules, but may be implemented utilizing any combination of dedicated hardware boards, DSPs, processors, etc. Alternatively, the system controller 104 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

During operation, a communication link 120 may transmit information (e.g. commands) to or receive information (e.g. data) from the biosensor 102 (FIG. 1) and/or the sub-systems 106, 108, 110 (FIG. 1). A communication link 122 may receive user input from the user interface 114 (FIG. 1) and transmit data or information to the user interface 114. Data from the biosensor 102 or sub-systems 106, 108, 110 may be processed by the system controller 104 in real-time during a bioassay session. Additionally or alternatively, data may be stored temporarily in a system memory during a bioassay session and processed in slower than real-time or off-line operation.

As shown in FIG. 2, the system controller 104 may include a plurality of modules 131-139 that communicate with a main control module 130. The main control module 130 may communicate with the user interface 114 (FIG. 1). Although the modules 131-139 are shown as communicating directly with the main control module 130, the modules 131-139 may also communicate directly with each other, the user interface 114, and the biosensor 102. Also, the modules 131-139 may communicate with the main control module 130 through the other modules.

The plurality of modules 131-139 include system modules 131-133, 139 that communicate with the sub-systems 106, 108, 110, and 111, respectively. The fluidic control module 131 may communicate with the fluidic control system 106 to control the valves and flow sensors of the fluid network for controlling the flow of one or more fluids through the fluid network. The fluid storage module 132 may notify the user when fluids are low or when the waste reservoir is at or near capacity. The fluid storage module 132 may also communicate with the temperature control module 133 so that the fluids may be stored at a desired temperature. The illumination module 139 may communicate with the illumination system 109 to illuminate the reaction sites at designated times during a protocol, such as after the desired reactions (e.g., binding events) have occurred.

The plurality of modules 131-139 may also include a device module 134 that communicates with the biosensor 102 and an identification module 135 that determines identification information relating to the biosensor 102. The device module 134 may, for example, communicate with the system receptacle 112 to confirm that the biosensor has established an electrical and fluidic connection with the bioassay system 100. The identification module 135 may receive signals that identify the biosensor 102. The identification module 135 may use the identity of the biosensor 102 to provide other information to the user. For example, the identification module 135 may determine and then display a lot number, a date of manufacture, or a protocol that is recommended to be run with the biosensor 102.

The plurality of modules 131-139 may also include a detection data analysis module 138 that receives and analyzes the signal data (e.g., image data) from the biosensor 102. The signal data may be stored for subsequent analysis or may be transmitted to the user interface 114 to display desired information to the user. In some embodiments, the signal data may be processed by the solid-state imager (e.g., CMOS image sensor) before the detection data analysis module 138 receives the signal data.

Protocol modules 136 and 137 communicate with the main control module 130 to control the operation of the sub-systems 106, 108, and 110 when conducting predetermined assay protocols. The protocol modules 136 and 137 may include sets of instructions for instructing the bioassay system 100 to perform specific operations pursuant to predetermined protocols. As shown, the protocol module may be a sequencing-by-synthesis (SBS) module 136 that is configured to issue various commands for performing sequencing-by-synthesis processes. In SBS, extension of a nucleic acid primer along a nucleic acid template is monitored to determine the sequence of nucleotides in the template. The underlying chemical process can be polymerization (e.g. as catalyzed by a polymerase enzyme) or ligation (e.g. catalyzed by a ligase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. For example, to initiate a first SBS cycle, commands can be given to deliver one or more labeled nucleotides, DNA polymerase, etc., into/through a flow cell that houses an array of nucleic acid templates. The nucleic acid templates may be located at corresponding reaction sites. Those reaction sites where primer extension causes a labeled nucleotide to be incorporated can be detected through an imaging event. During an imaging event, the illumination system 111 may provide an excitation light to the reaction sites. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination a command can be given to deliver a deblocking reagent to the flow cell (before or after detection occurs). One or more commands can be given to effect wash(es) between the various delivery steps. The cycle can then be repeated n times to extend the primer by n nucleotides, thereby detecting a sequence of length n. Exemplary sequencing techniques are described, for example, in Bentley et al., Nature 456:53-59 (2008), WO 04/018497; U.S. Pat. No. 7,057,026; WO 91/06678; WO 07/123,744; U.S. Pat. No. 7,329,492; U.S. Pat. No. 7,211,414; U.S. Pat. No. 7,315,019; U.S. Pat. No. 7,405,281, and US 2008/0108082, each of which is incorporated herein by reference.

For the nucleotide delivery step of an SBS cycle, either a single type of nucleotide can be delivered at a time, or multiple different nucleotide types (e.g. A, C, T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, an excitation source need only provide excitation at a single wavelength or in a single range of wavelengths. For a nucleotide delivery configuration where delivery results in multiple different nucleotides being present in the flow cell at one time, sites that incorporate different nucleotide types can be distinguished based on different fluorescent labels that are attached to respective nucleotide types in the mixture. For example, four different nucleotides can be used, each having one of four different fluorophores. In one embodiment, the four different fluorophores can be distinguished using excitation in four different regions of the spectrum. For example, four different excitation radiation sources can be used. Alternatively, fewer than four different excitation sources can be used, but optical filtration of the excitation radiation from a single source can be used to produce different ranges of excitation radiation at the flow cell.

In some embodiments, fewer than four different colors can be detected in a mixture having four different nucleotides. For example, pairs of nucleotides can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. Exemplary apparatus and methods for distinguishing four different nucleotides using detection of fewer than four colors are described for example in U.S. Pat. App. Ser. Nos. 61/538,294 and 61/619,878, which are incorporated herein by reference their entireties. U.S. application Ser. No. 13/624,200, which was filed on Sep. 21, 2012, is also incorporated by reference in its entirety.

The plurality of protocol modules may also include a sample-preparation (or generation) module 137 that is configured to issue commands to the fluidic control system 106 and the temperature control system 110 for amplifying a product within the biosensor 102. For example, the biosensor 102 may be engaged to the bioassay system 100. The amplification module 137 may issue instructions to the fluidic control system 106 to deliver necessary amplification components to reaction chambers within the biosensor 102. In other embodiments, the reaction sites may already contain some components for amplification, such as the template DNA and/or primers. After delivering the amplification components to the reaction chambers, the amplification module 137 may instruct the temperature control system 110 to cycle through different temperature stages according to known amplification protocols. In some embodiments, the amplification and/or nucleotide incorporation is performed isothermally.

The SBS module 136 may issue commands to perform bridge PCR where clusters of clonal amplicons are formed on localized areas within a channel of a flow cell. After generating the amplicons through bridge PCR, the amplicons may be "linearized" to make single stranded template DNA, or sstDNA, and a sequencing primer may be hybridized to a universal sequence that flanks a region of interest. For example, a reversible terminator-based sequencing by synthesis method can be used as set forth above or as follows.

Each sequencing cycle can extend a sstDNA by a single base which can be accomplished for example by using a modified DNA polymerase and a mixture of four types of nucleotides. The different types of nucleotides can have unique fluorescent labels, and each nucleotide can further have a reversible terminator that allows only a single-base incorporation to occur in each cycle. After a single base is added to the sstDNA, excitation light may be incident upon the reaction sites and fluorescent emissions may be detected. After detection, the fluorescent label and the terminator may be chemically cleaved from the sstDNA. Another similar sequencing cycle may follow. In such a sequencing protocol, the SBS module 136 may instruct the fluidic control system 106 to direct a flow of reagent and enzyme solutions through the biosensor 102. Exemplary reversible terminator-based SBS methods which can be utilized with the apparatus and methods set forth herein are described in US Patent Application Publication No. 2007/0166705 A1, US Patent Application Publication No. 2006/0188901 A1, U.S. Pat. No.

7,057,026, US Patent Application Publication No. 2006/0240439 A1, US Patent Application Publication No. 2006/0281109 A1, PCT Publication No. WO 05/065814, US Patent Application Publication No. 2005/0100900 A1, PCT Publication No. WO 06/064199 and PCT Publication No. WO 07/010,251, each of which is incorporated herein by reference in its entirety. Exemplary reagents for reversible terminator-based SBS are described in U.S. Pat. No. 7,541,444; U.S. Pat. No. 7,057,026; U.S. Pat. No. 7,414,116; U.S. Pat. No. 7,427,673; U.S. Pat. No. 7,566,537; U.S. Pat. No. 7,592,435 and WO 07/135,368, each of which is incorporated herein by reference in its entirety.

In some embodiments, the amplification and SBS modules may operate in a single assay protocol where, for example, template nucleic acid is amplified and subsequently sequenced within the same cartridge.

The bioassay system 100 may also allow the user to reconfigure an assay protocol. For example, the bioassay system 100 may offer options to the user through the user interface 114 for modifying the determined protocol. For example, if it is determined that the biosensor 102 is to be used for amplification, the bioassay system 100 may request a temperature for the annealing cycle. Furthermore, the bioassay system 100 may issue warnings to a user if a user has provided user inputs that are generally not acceptable for the selected assay protocol.

Figure 3:
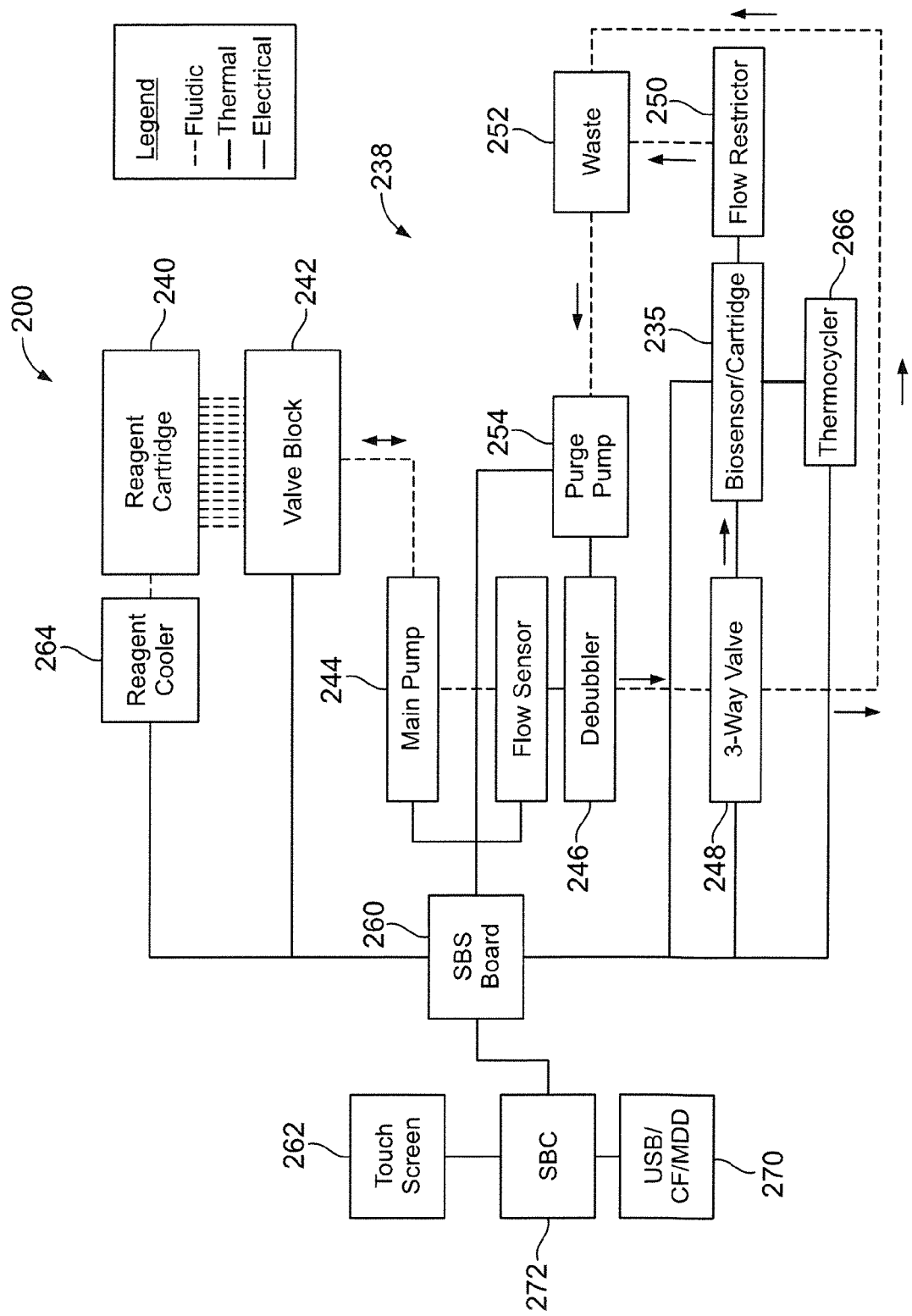
FIG. 3 is a block diagram of an exemplary workstation for biological or chemical analysis in accordance with one embodiment.

FIG. 3 is a block diagram of an exemplary workstation 200 for biological or chemical analysis in accordance with one embodiment. The workstation 200 may have similar features, systems, and assemblies as the bioassay system 100 described above. For example, the workstation 200 may have a fluidic control system, such as the fluidic control system 106 (FIG. 1), that is fluidicly coupled to a biosensor (or cartridge) 235 through a fluid network 238. The fluid network 238 may include a reagent cartridge 240, a valve block 242, a main pump 244, a debubbler 246, a 3-way valve 248, a flow restrictor 250, a waste removal system 252, and a purge pump 254. In particular embodiments, most of the components or all of the components described above are within a common workstation housing (not shown). Although not shown, the workstation 200 may also include an illumination system, such as the illumination system 111, that is configured to provide an excitation light to the reaction sites.

A flow of fluid is indicated by arrows along the fluid network 238. For example, reagent solutions may be removed from the reagent cartridge 240 and flow through the valve block 242. The valve block 242 may facilitate creating a zero-dead volume of the fluid flowing to the cartridge 235 from the reagent cartridge 240. The valve block 242 can select or permit one or more liquids within the reagent cartridge 240 to flow through the fluid network 238. For example, the valve block 242 can include solenoid valves that have a compact arrangement. Each solenoid valve can control the flow of a fluid from a single reservoir bag. In some embodiments, the valve block 242 can permit two or more different liquids to flow into the fluid network 238 at the same time thereby mixing the two or more different liquids. After leaving the valve block 242, the fluid may flow through the main pump 244 and to the debubbler 246. The debubbler 246 is configured to remove unwanted gases that have entered or been generated within the fluid network 238.

From the debubbler 246, fluid may flow to the 3-way valve 248 where the fluid is either directed to the cartridge 235 or bypassed to the waste removal system 252. A flow of the fluid within the cartridge 235 may be at least partially controlled by the flow restrictor 250 located downstream from the cartridge 235. Furthermore, the flow restrictor 250 and the main pump 244 may coordinate with each other to control the flow of fluid across reaction sites and/or control the pressure within the fluid network 238. Fluid may flow through the cartridge 235 and onto the waste removal system 252. Optionally, fluid may flow through the purge pump 254 and into, for example, a waste reservoir bag within the reagent cartridge 240.

Also shown in FIG. 3, the workstation 200 may include a temperature control system, such as the temperature control system 110, that is configured to regulate or control a thermal environment of the different components and sub-systems of the workstation 200. The temperature control system 110 can include a reagent cooler 264 that is configured to control the temperature requirements of various fluids used by the workstation 200, and a thermocycler 266 that is configured to control the temperature of a cartridge 235. The thermocycler 266 can include a thermal element (not shown) that interfaces with the cartridge.

Furthermore, the workstation 200 may include a system controller or SBS board 260 that may have similar features as the system controller 104 described above. The SBS board 260 may communicate with the various components and sub-systems of the workstation 200 as well as the cartridge 235. Furthermore, the SBS board 260 may communicate with remote systems to, for example, store data or receive commands from the remote systems. The workstation 200 may also include a touch screen user interface 262 that is operatively coupled to the SBS board 260 through a single-board computer (SBC) 272. The workstation 200 may also include one or more user accessible data communication ports and/or drives. For example a workstation 200 may include one or more universal serial bus (USB) connections for computer peripherals, such as a flash or jump drive, a compact-flash (CF) drive and/or a hard drive 270 for storing user data in addition to other software.

Figure 4:
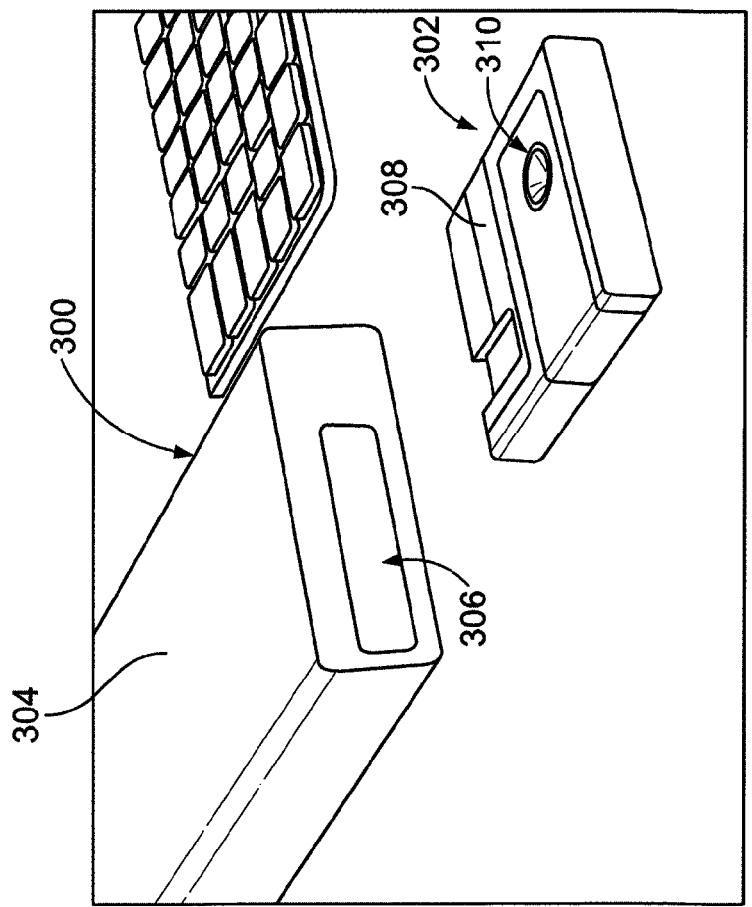
FIG. 4 is a perspective view of an exemplary workstation and an exemplary cartridge in accordance with one embodiment.

FIG. 4 is a perspective view of a workstation 300 and a cartridge 302 that may include one or more biosensors (not shown) as described herein. The workstation 300 may include similar components as described above with respect to the bioassay system 100 and the workstation 200 and may operate in a similar manner. For example, the workstation 300 may include a workstation housing 304 and a system receptacle 306 that is configured to receive and engage the cartridge 302. The system receptacle may at least one of fluidically or electrically engage the cartridge 302. The workstation housing 304 may hold, for example, a system controller, a fluid storage system, a fluidic control system, and a temperature control system as described above. In FIG. 4, the workstation 300 does not include a user interface or display that is coupled to the workstation housing 304. However, a user interface may be communicatively coupled to the housing 304 (and the components/systems therein) through a communication link. Thus, the user interface and the workstation 300 may be remotely located with respect to each other. Together, the user interface and the workstation 300 (or a plurality of workstations) may constitute a bioassay system.

As shown, the cartridge 302 includes a cartridge housing 308 having at least one port 310 that provides access to an interior of the cartridge housing 308. For example, a solution that is configured to be used in the cartridge 302 during the controlled reactions may be inserted through the port 310 by a technician or by the workstation 300. The system receptacle 306 and the cartridge 302 may be sized and shaped relative to each other such that the cartridge 302 may be inserted into a receptacle cavity (not shown) of the system receptacle 306.

Figure 5:
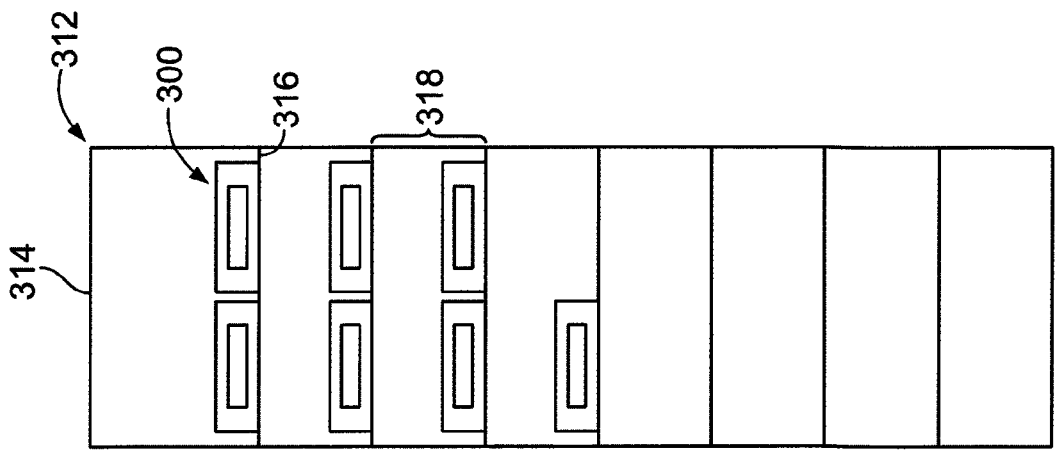
FIG. 5 is a front view of an exemplary rack assembly that includes a plurality of the workstations of FIG. 4.

FIG. 5 is a front view of a rack assembly 312 having a cabinet or carriage 314 with a plurality of the workstations 300 loaded thereon. The cabinet 314 may include one or more shelves 316 that define one or more reception spaces 318 configured to receive one or more workstations 300. Although not shown, the workstations 300 may be communicatively coupled to a communication network that permits a user to control operation of the workstations 300. In some embodiments, a bioassay system includes a plurality of workstations, such as the workstations 300, and a single user interface configured to control operation of the multiple workstations.

Figure 6:
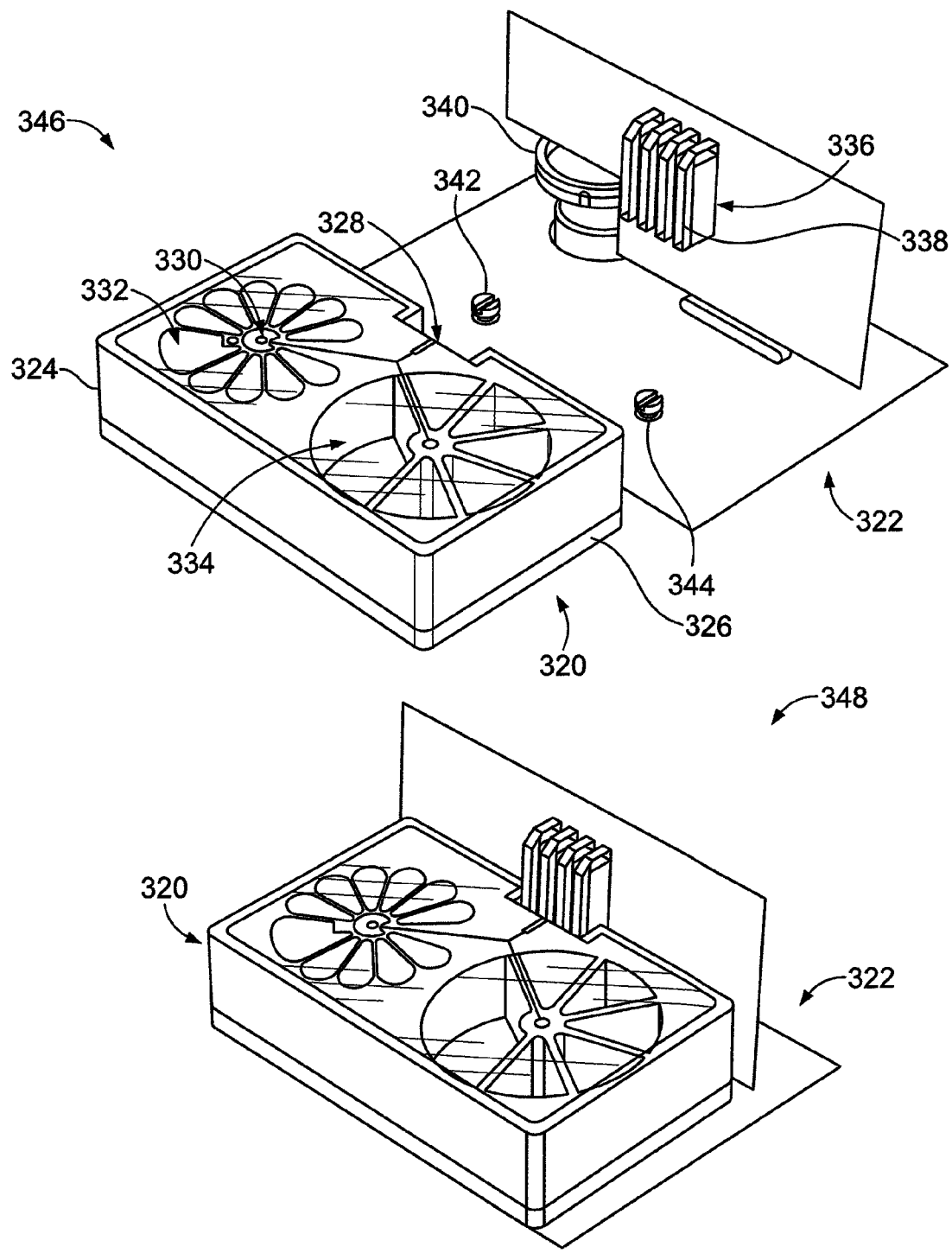
FIG. 6 illustrates internal components of an exemplary cartridge.

FIG. 6 illustrates various features of the cartridge 302 (FIG. 4) in accordance with one embodiment. As shown, the cartridge 302 may include a sample assembly 320, and the system receptacle 306 may include a light assembly 322. Stage 346 shown in FIG. 6 represents the spatial relationship between the first and second sub-assemblies 320 and 322 when they are separate from each other. At stage 348, the first and second sub-assemblies 320 and 322 are joined together. The cartridge housing 308 (FIG. 4) may enclose the joined first and second sub-assemblies 320 and 322.

In the illustrated embodiment, the first sub-assembly 320 includes a base 326 and a reaction-component body 324 that is mounted onto the base 326. Although not shown, one or more biosensors may be mounted to the base 326 in a recess 328 that is defined, at least in part, by the reaction-component body 324 and the base 326. For example, at least four biosensors may be mounted to the base 326. In some embodiments, the base 326 is a printed circuit board having circuitry that enables communication between the different components of the cartridge and the workstation 300 (FIG. 4). For example, the reaction-component body 324 may include a rotary valve 330 and reagent reservoirs 332 that are fluidically coupled to the rotary valve 330. The reaction-component body 324 may also include additional reservoirs 334.

The second sub-assembly 322 includes a light assembly 336 that includes a plurality of light directing channels 338. Each light directing channel 338 is optically coupled to a light source (not shown), such as a light-emitting diode (LED). The light source(s) are configured to provide an excitation light that is directed by the light directing channels 338 onto the biosensors. In alternative embodiments, the cartridge may not include a light source(s). In such embodiments, the light source(s) may be located in the workstation 300. When the cartridge is inserted into the system receptacle 306 (FIG. 4), the cartridge 302 may align with the light source(s) so that the biosensors may be illuminated.

Also shown in FIG. 6, the second sub-assembly 322 includes a cartridge pump 340 that is fluidically coupled to ports 342 and 344. When the first and second sub-assemblies 320 and 322 are joined together, the port 342 is coupled to the rotary valve 330 and the port 344 is coupled to the other reservoirs 334. The cartridge pump 340 may be activated to direct reaction components from the reservoirs 332 and/or 334 to the biosensors according to a designated protocol.

Figure 7:
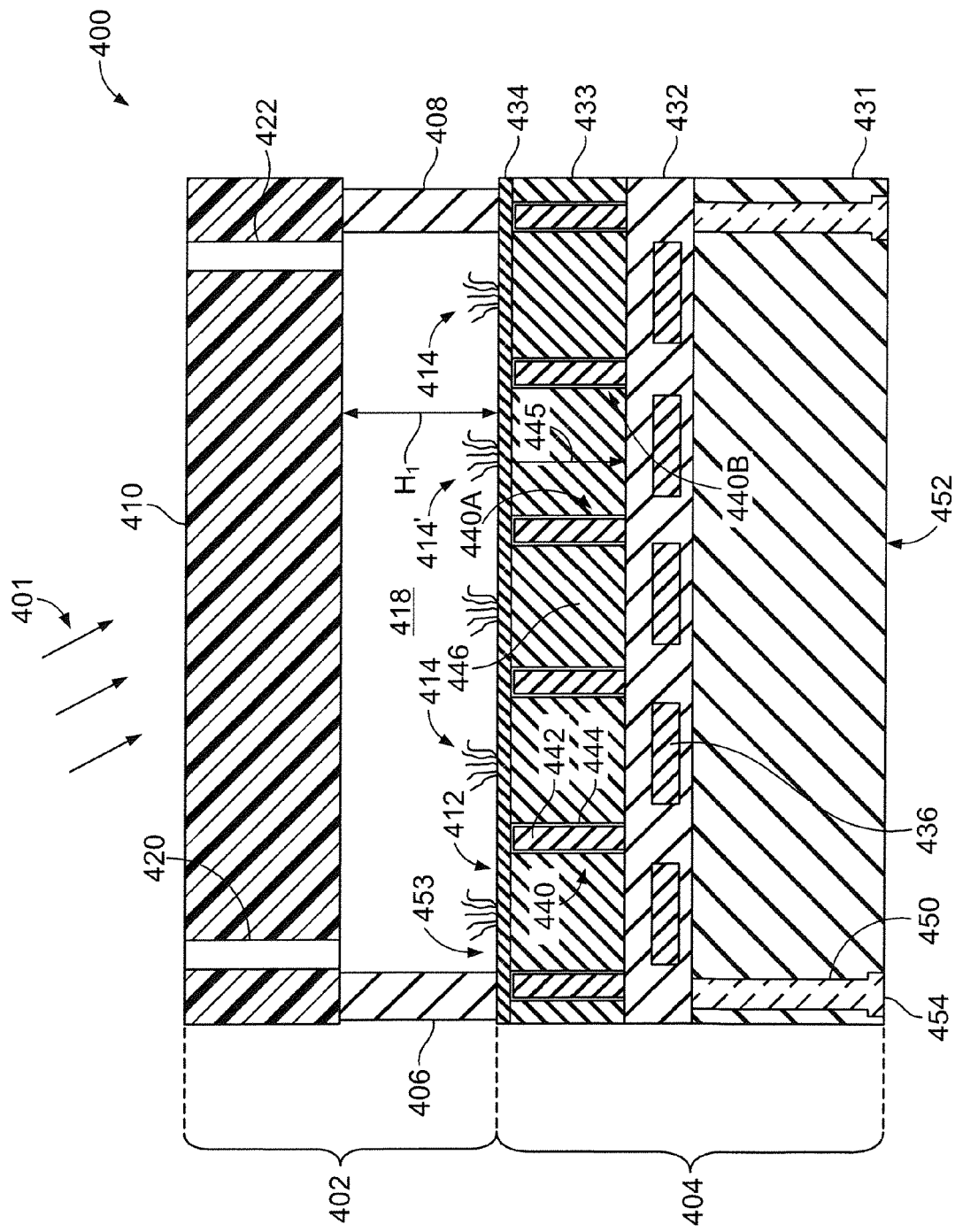
FIG. 7 illustrates a cross-section of an exemplary biosensor formed in accordance with one embodiment.

FIG. 7 illustrates a cross-section of an exemplary biosensor 400 formed in accordance with one embodiment. The biosensor 400 may have similar features as the biosensor 102 (FIG. 1) described above and may be used in, for example, the cartridge 302 (FIG. 4). As shown, the biosensor 400 may include a flow cell 402 that is mounted onto a detection device 404. In the illustrated embodiment, the flow cell 402 is affixed directly to the detection device 404. However, in alternative embodiments, the flow cell 402 may be removably coupled to the detection device 404. The detection device 404 has a detector surface 412 that may be functionalized (e.g., chemically or physically modified in a suitable manner for conducting the desired reactions). For example, the detector surface 412 may be functionalized and may include a plurality of reaction sites 414 having one or more biomolecules immobilized thereto. In the illustrated embodiment, the flow cell 402 includes sidewalls 406, 408 and a flow cover 410 that is supported by the sidewalls 406, 408. The sidewalls 406, 408 are coupled to the detector surface 412 and extend between the flow cover 410 and the sidewalls 406, 408. In some embodiments, the sidewalls 406, 408 are formed from a curable adhesive layer that bonds the flow cover 410 to the detection device 404.

The sidewalls 406, 408 are sized and shaped so that a flow channel 418 exists between the flow cover 410 and the detection device 404. As shown, the flow channel 418 may include a height $H_1$ that is determined by the sidewalls 406, 408. The height $H_1$ may be between about 50-400 μm (microns) or, more particularly, about 80-200 μm. In the illustrated embodiment, the height $H_1$ is about 100 μm. The flow cover 410 may include a material that is transparent to excitation light 401 propagating from an exterior of the biosensor 400 into the flow channel 418. As shown in FIG. 7, the excitation light 401 approaches the flow cover 410 at a non-orthogonal angle. However, this is only for illustrative purposes as the excitation light 401 may approach the flow cover 410 from different angles.

Also shown, the flow cover 410 may include inlet and outlet ports 420, 422 that are configured to fluidically engage other ports (not shown). For example, the other ports may be from the cartridge 302 (FIG. 4) or the workstation 300 (FIG. 4). The flow channel 418 is sized and shaped to direct a fluid along the detector surface 412. The height $H_1$ and other dimensions of the flow channel 418 may be configured to maintain a substantially even flow of a fluid along the detector surface 412. The dimensions of the flow channel 418 may also be configured to control bubble formation.

As shown in exemplary FIG. 7, the sidewalls 406, 408 and the flow cover 410 are separate components that are coupled to each other. In alternative embodiments, the sidewalls 406, 408 and the flow cover 410 may be integrally formed such that the sidewalls 406, 408 and the flow cover 410 are formed from a continuous piece of material. By way of example, the flow cover 410 (or the flow cell 402) may comprise a transparent material, such as glass or plastic. The flow cover 410 may constitute a substantially rectangular block having a planar exterior surface and a planar inner surface that defines the flow channel 418. The block may be mounted onto the sidewalls 406, 408. Alternatively, the flow cell 402 may be etched to define the flow cover 410 and the sidewalls 406, 408. For example, a recess may be etched into the transparent material. When the etched material is mounted to the detection device 404, the recess may become the flow channel 418.

The detector surface 412 may be substantially planar as shown in FIG. 7. However, in alternative embodiments, the detector surface 412 may be shaped to define reaction chambers in which each reaction chamber has one or more reaction sites 414. The reaction chambers may be defined by, for example, chamber walls that effectively separate the reaction site(s) 414 of one reaction chamber from the reaction site(s) 414 of an adjacent reaction chamber.

As shown in FIG. 7, the reaction sites 414 may be distributed in a pattern along the detector surface 412. For example, the reactions sites 414 may be located in rows and columns along the detector surface 412 in a manner that is similar to a microarray. However, it is understood that various patterns of reaction sites may be used. In particular embodiments, the reaction sites 414 include clusters or colonies of biomolecules (e.g., oligonucleotides) that are immobilized on the detector surface 412.

The detection device 404 may be similar to, for example, an integrated circuit comprising a plurality of stacked substrate layers 431-434. The substrate layers 431-434 may include a base substrate 431, a solid-state imager 432 (e.g., CMOS image sensor), a filter or light-management layer 433, and a passivation layer 434. It should be noted that the above is only illustrative and that other embodiments may include fewer or additional layers. Moreover, each of the substrate layers 431-434 may include a plurality of sublayers. As will be described in greater detail below, the detection device 404 may be manufactured using processes that are similar to those used in manufacturing integrated circuits, such as CMOS image sensors and CCDs. For example, the substrate layers 431-434 or portions thereof may be grown, deposited, etched, and the like to form the detection device 404.

The passivation layer 434 is configured to shield the filter layer 433 from the fluidic environment of the flow channel 418. In some cases, the passivation layer 434 is also configured to provide a solid surface (i.e., the detector surface 412) that permits biomolecules or other analytes-of-interest to be immobilized thereon. For example, each of the reaction sites 414 may include a cluster of biomolecules that are immobilized to the detector surface 412. Thus, the passivation layer 434 may be formed from a material that permits the reaction sites 414 to be immobilized thereto. The passivation layer 434 may also comprise a material that is at least transparent to a desired fluorescent light. By way of example, the passivation layer 434 may include silicon nitride ($Si_3N_4$) and/or silica ($SiO_2$). However, other suitable material(s) may be used. In the illustrated embodiment, the passivation layer 434 may be substantially planar. However, in alternative embodiments, the passivation layer 434 may include recesses, such as pits, wells, grooves, and the like. In the illustrated embodiment, the passivation layer 434 has a thickness that is about 150-200 nm and, more particularly, about 170 nm.

The filter layer 433 may include various features that affect the transmission of light. In some embodiments, the filter layer 433 can perform multiple functions. For instance, the filter layer 433 may be configured to (a) filter unwanted light signals, such as light signals from an excitation light source; (b) direct emission signals from the reaction sites 414 toward corresponding light detectors 436 that are configured to detect the emission signals from the reaction sites; or (c) block or prevent detection of unwanted emission signals from adjacent reaction sites. As such, the filter layer 433 may also be referred to as a light-management layer. In the illustrated embodiment, the filter layer 433 has a thickness that is about 1-5 µm and, more particularly, about 3-4 µm.

In some embodiments, the filter layer 433 may include a plurality of filter walls 440. The filter walls 440 may be configured to at least one of (a) reflect emission signals or (b) block or prevent unwanted emissions signals from adjacent reaction sites. As will be described in greater detail below, adjacent filter walls 440, such as filter walls 440A, 440B, may define a detection path 445 for the emission signals that are provided by the reaction site 414'. The detection path 445 extends between the detector surface 412 to a light detector 436, which is described in greater detail below. The filter walls 440 may be formed from various kinds of materials. For example, the filter walls 440 may include an internal material 442 (e.g., glass) and an exterior coating 444 that is deposited onto surfaces of the internal material 442. In the illustrated embodiment, the coating 444 includes a reflective metal (e.g., aluminum). In alternative embodiments, the coating 444 may include a dielectric material.

Also shown, a light-absorbing material 446 may be deposited between adjacent filter walls 440. The light-absorbing material 446 may include, for example, a material that is configured to absorb the excitation light and permit the fluorescent emissions (i.e., emission light, emission signals) to pass therethrough. In the illustrated embodiment, the light-absorbing material 446 may comprise a resist-based absorption material that is configured to block, for example, 532 nm excitation light. However, other light-absorbing materials 446 may be used. In alternative embodiments, a dichroic filter may be positioned between adjacent filter walls 440. In other alternative embodiments, a dichroic filter layer is located above or below the filter walls 440. For example, the dichroic filter layer may be located between the passivation layer 434 and the filter layer 433.

In alternative embodiments, the filter layer 433 may include an array of microlenses or other optical components. Each of the microlenses may be configured to direct emission signals from an associated reaction site 414 to an associated light detector 436. Such microlenses may be used in addition to or as an alternative to the filter walls 440.

In some embodiments, the solid-state imager 432 and the base substrate 431 may be provided together as a previously constructed solid-state imaging device (e.g., CMOS chip). For example, the base substrate 431 may be a wafer of silicon and the solid-state imager 432 may be mounted thereon. The solid-state imager 432 includes a layer of semiconductor material (e.g., silicon) and the light detectors 436. In some embodiments, each light detector 436 is formed from a single pixel. In other embodiments, multiple pixels (e.g., 2, 3, 4, 5, 6, or more) may form a single light detector 436. In the illustrated embodiment, the light detector 436 pixels are photodiodes configured to detect light.

The solid-state imager 432 may include a dense array of light detectors 436 that are configured to detect activity indicative of a desired reaction from within or along the flow channel 418. In some embodiments, each light detector 436 has a detection area that is less than about 50 µm². In particular embodiments, the detection area is less than about 10 µm². In more particular embodiments, the detection area is about 2 µm². In such cases, the light detector 436 may constitute a single pixel. An average read noise of each pixel in a light detector 436 may be, for example, less than about 150 electrons. In more particular embodiments, the read noise may be less than about 5 electrons. The resolution of the array of light detectors 436 may be greater than about 0.5 megapixels (Mpixels). In more specific embodiments, the resolution may be greater than about 5 Mpixels and, more particularly, greater than about 10 Mpixels.

In some embodiments, the detection device 404 includes a microcircuit arrangement, such as the microcircuit arrangement described in U.S. Pat. No. 7,595,883, which is incorporated herein by reference in the entirety. More specifically, the detection device 404 may comprise an integrated circuit having a planar array of the light detectors 436. Circuitry formed within the detection device 404 may be configured for at least one of signal amplification, digitization, storage, and processing. The circuitry may collect and analyze the detected fluorescent light and generate data signals for communicating detection data to a bioassay system. The circuitry may also perform additional analog and/or digital signal processing in the detection device 404. The circuitry may include conductive vias 450 that transmit the data signals to a bottom side 452 of the biosensor 400. The data signals may be transmitted through electrical contacts 454 of the biosensor 400. By transmitting the data signals to the bottom side 452 instead of a top side 453, the biosensor 400 may be permitted to use more area of the top side 453 for detecting fluorescent light.

Figure 8:
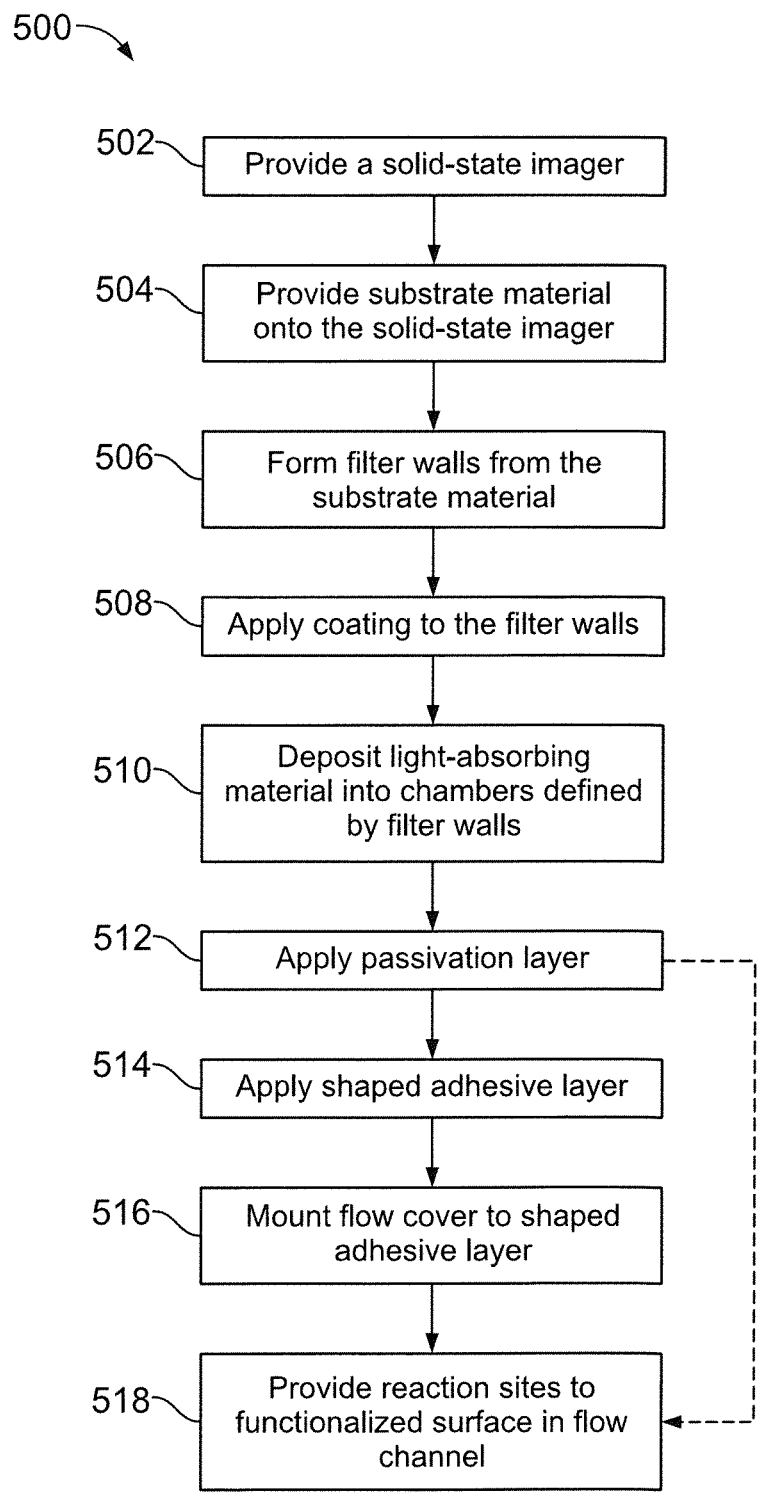
FIG. 8 is a flowchart illustrating an exemplary method of manufacturing the biosensor of FIG. 7.

FIG. 8 is a flowchart illustrating a method or workflow 500 of manufacturing the biosensor 400 shown in FIG. 7. However, it should be noted that the method 500 is only one example of manufacturing the biosensor 400 and others may be used. FIGS. 9-15 illustrate the biosensor 400 at different manufacturing stages throughout the workflow. The method 500 includes providing at 502 the solid-state imager 432. The providing operation 502 may include providing the solid-state imager 432 with the base substrate 431 attached thereto. For example, in some embodiments, the solid-state imager 432 and the base substrate 431 may be provided as a previously-manufactured unit and the remainder of the biosensor 400 constructed thereon. In other embodiments, the providing operation 502 includes manufacturing the base substrate 431 and the solid-state imager 432 thereon using integrated circuit manufacturing processes. More specifically, the base substrate 431 and the solid-state imager 432 may be manufactured by, for example, growing, depositing, and etching various layers and features in the layers (e.g., the light detectors 436). In particular, the solid-state imager 432 is an image sensor that is manufactured using processes similar to complementary metal-oxide-semiconductor (CMOS) technology. The remaining layers 433 and 434 may also be manufactured using integrated circuit manufacturing processes.

Figure 9:
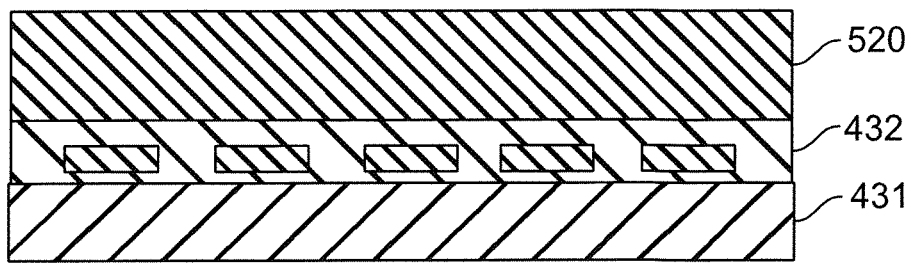
FIGS. 9-16 illustrate the biosensor of FIG. 7 at different manufacturing stages.
Figure 10:
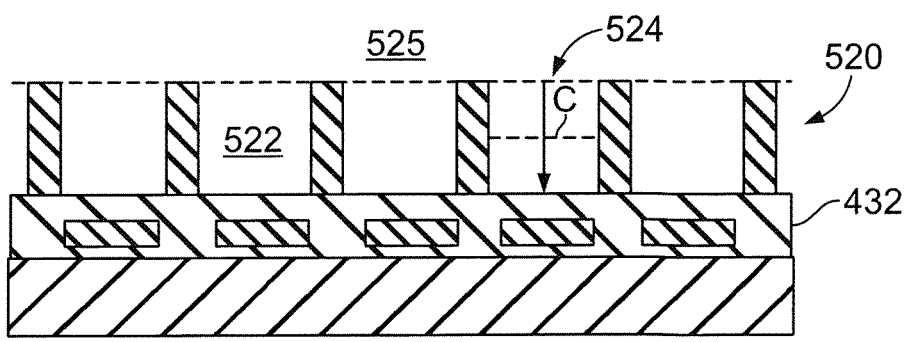

At 504, a substrate material 520 may be provided onto the solid-state imager 432 as shown in FIG. 9. The substrate material 520 may be grown or deposited onto the solid-state imager 432. In particular embodiments, the substrate material 520 includes glass or plastic. However, alternative materials that are capable of being formed as described herein may also be used. With respect to FIG. 10, the method 500 may also include forming at 506 the filter walls 440 from the substrate material 520. The forming operation 506 may include removing (e.g., through etching) portions of the substrate material 520 to form the filter walls 440. As shown in FIG. 10, chambers 522 may be formed at 506 that are defined by the filter walls 440 and the adjacent layer 432, which is the solid-state imager 432 in the illustrated embodiment.

FIG. 10 shows a side cross-sectional view of the chambers 522. The chambers 522 include a chamber opening 524 that provides access to the chamber 522 from the ambient environment or exterior 525 above. The chambers 522 may constitute channels or recesses that extend from the respective chamber openings 524 to the solid-state imager 432. A cross-section C of the chamber 522 taken perpendicular to the arrow in FIG. 10 may have various shapes. For example, the cross-section C may be polygonal (e.g., rectangular, pentagonal, and the like) or substantially circular. In the illustrated embodiment, the cross-section of the channel is square-shaped.

Figure 11:
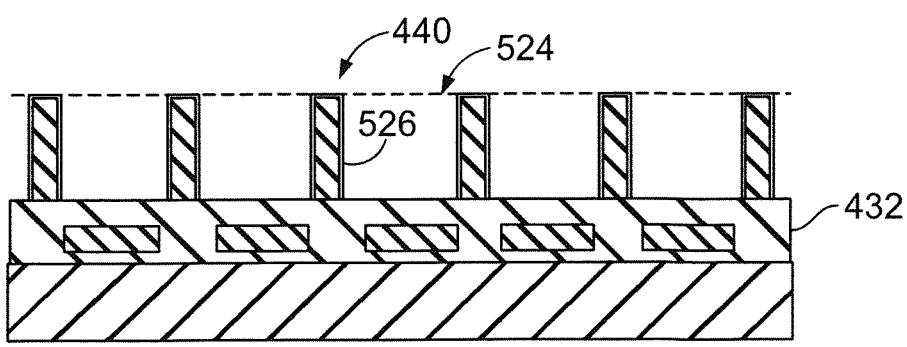
Figure 16:
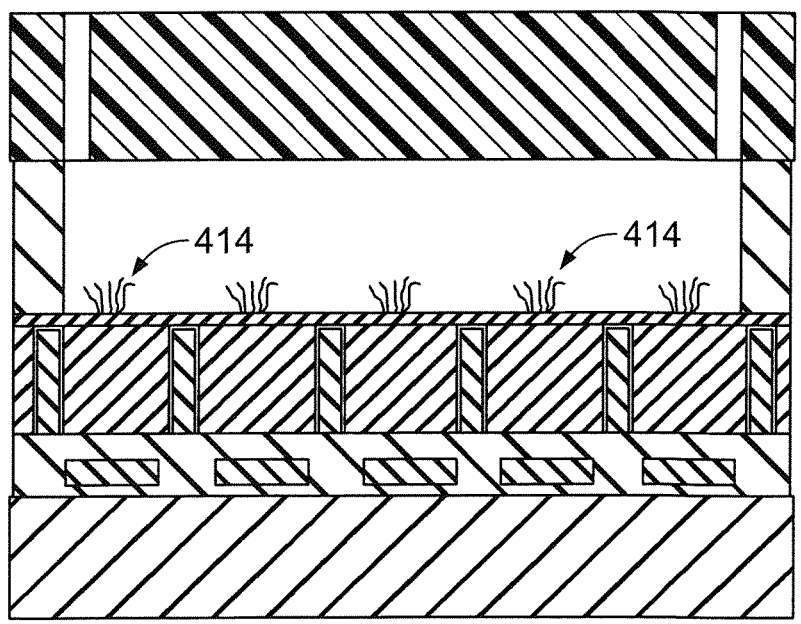

A coating 526 may be applied at 508 to the filter walls 440 as shown in FIG. 11. Various materials for the coating 526 may be used. For instance, when the biosensor 400 (FIG. 7) is fully constructed, the coating 526 is configured to reflect light emissions that propagate through the chamber opening 524 toward the solid-state imager 432. As such, the coating 526 may be any material that is capable of being coated onto the filter wall 440 and that is also capable of reflecting the light emissions. By way of example, the coating 526 may include a metal, such as aluminum. Alternatively, the coating 526 may be a dielectric material having an index of refraction that is less than the index of refraction of the light-absorbing material 446. The coating 526 may extend entirely around the filter walls 440 as shown in FIG. 11 or, as will be described in greater detail below with respect to FIG. 16, the coating 526 may be located on only portions of the filter walls 440. Although not shown, during the applying operation 508 the coating 526 may also be deposited onto the solid-state imager 432. In such cases, the coating 526 on the solid-state imager 432 may be removed (e.g., through etching).

Figure 12:
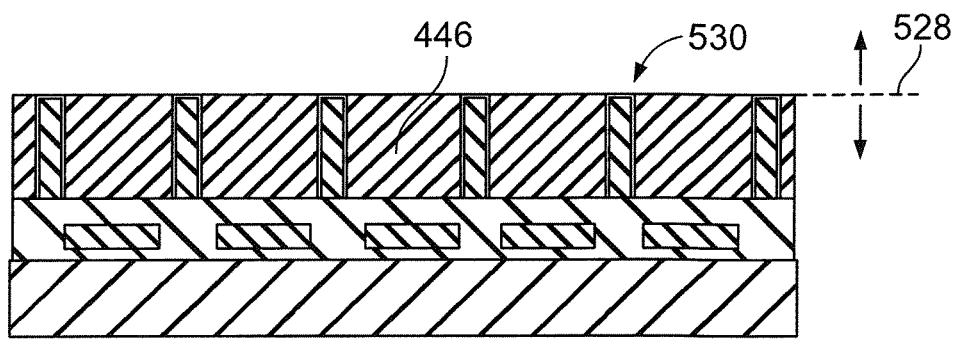

The method 500 also includes depositing or applying at 510 the light-absorbing material 446 into the chambers 522 (FIG. 10). As shown in FIG. 12, the light-absorbing material 446 extends to a fill line 528 that is substantially flush with ends 530 of the filter walls 440. However, as indicated by the arrows, the fill line 528 may have other heights. For example, the fill line 528 may clear the ends 530 such that the ends 530 are located a depth within the light-absorbing material 446. The fill line 528 may also be located a depth below the ends 530 such that a portion of the chamber 522 remains unfilled. In such embodiments, the unfilled portions of the chambers 522 may at least partially define reaction chambers as described herein.

Figure 13:
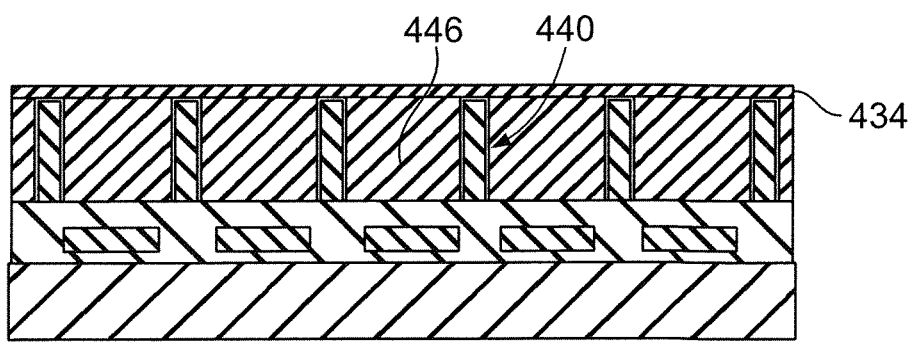

The passivation layer 434 may be applied (e.g., deposited) at 512 onto the light-absorbing material 446 as shown in FIG. 13. In such embodiments in which an unfilled chamber portion remains after the depositing operation 508, the applying operation 512 may include inserting passivation material into the unfilled chamber portions so that reaction chambers are formed. Such reaction chambers may be defined entirely by the passivation material or by a portion of the passivation material and the filter walls 440 (e.g., the filter walls 440 may clear and project beyond the passivation layer 434). In other embodiments, the unfilled chamber portions may be filled entirely by the passivation material so that the filter walls 440 are substantially flush with the passivation layer 443.

Figure 14:
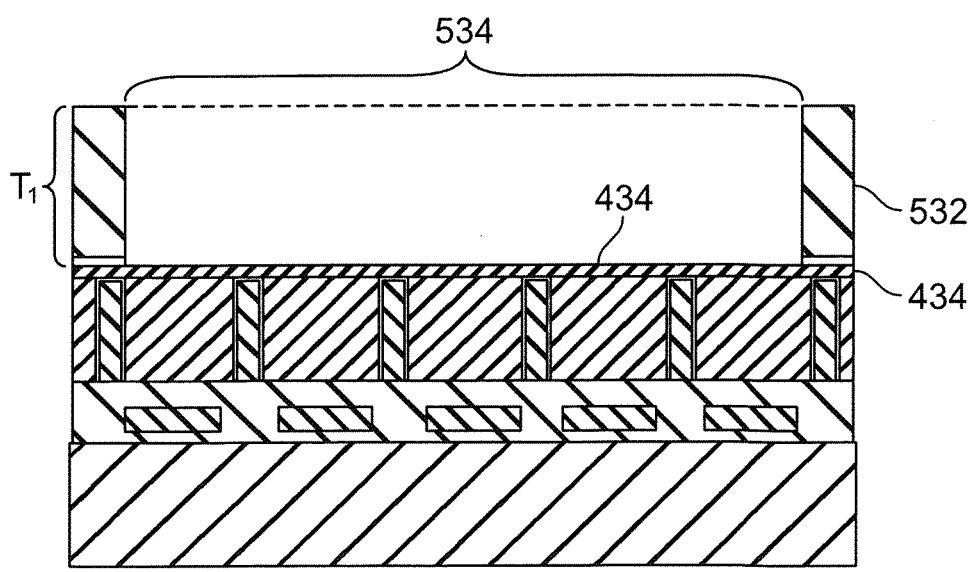
Figure 15:
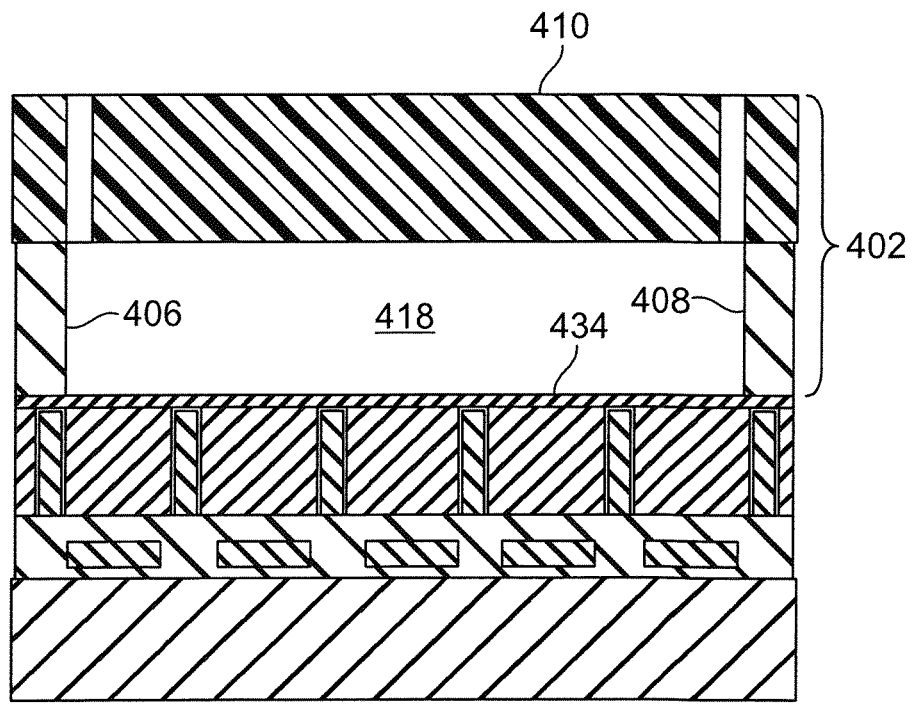

In some embodiments, the method 500 may also include applying at 514 a shaped adhesive strip or layer 532 (shown in FIG. 14, also illustrated in FIG. 7 as the sidewalls as further described below) onto the passivation layer 434. The flow cover 410 (shown in FIG. 15) may then be mounted to the adhesive layer 532. In FIG. 14, the adhesive layer 532 is a single sheet of material that is shaped to include an opening 534. However, in alternative embodiments, multiple layer sections may be deposited onto the passivation layer 434 that effectively define the opening 534. With the flow cover 410 mounted onto the adhesive layer 532, the adhesive layer 532 may then be cured or hardened to affix the flow cover 410 and the adhesive layer 532 to the passivation layer 434 thereby forming the flow cell 402. The adhesive layer 532 defines the sidewalls 406, 408. In some embodiments, the adhesive layer 532 comprises a photopolymer that is cured when exposed to ultraviolet or visible light. As shown in FIG. 14, the adhesive layer 532 may have a thickness $T_1$ that is substantially equal to the height $H_1$ of the flow channel 418.

Optionally, the method 500 may also include providing at 518 the reaction sites 414 onto the passivation layer 434. Although the providing operation 518 is shown in FIG. 8 as occurring after the operations 514 and 516, the providing operation 518 may occur after or during the application of the passivation layer 434. For example, the applying operation 512 may include coupling the passivation layer 434 onto the filter layer 433 (or another layer in alternative embodiments), wherein the passivation layer 434 includes previously fabricated pads that are configured to have analytes-of-interest immobilized thereon. In other embodiments, after the passivation layer 512 is applied (and before the adhesive layer and flow cover are coupled to the detection device), the reaction sites or portions thereof may be patterned onto the passivation layer 512. For example, the reaction sites may include pads or metal regions that are described in U.S. Provisional Application No. 61/495,266, filed on Jun. 9, 2011, and U.S. Provisional Application No. 61/552,712, filed on Oct. 28, 2011. Each of the U.S. Provisional Application No. 61/495,266 (the '266 Application) and the U.S. Provisional Application No. 61/552,712 (the '712 Application) is incorporated herein by reference in its entirety. In some embodiments, the reaction sites 414 may be fabricated after the flow cell 402 is manufactured on the detection device 404.

The incorporated '712 Application describes techniques for preparing an array of reaction sites. Exemplary techniques of the '712 Application are illustrated by FIGS. 17-28. In some embodiments, each of the reaction sites is particularly suited for capturing a single molecule of interest at the reaction site. Once the molecule has been captured at the reaction site, the molecule may be amplified to provide a plurality of molecules (e.g., cluster) having the same chemical structure at the reaction site. For example, FIG. 17 generally represents certain phases included in the preparation of the reaction sites on a detector surface, such as the detector surface 412. As described above, the passivation layer 434 may be any one or more of various types of material that are capable of shielding or protecting the circuitry from fluids and reactants used in an analytical detection procedure. For example, the passivation layer 434 may include polymeric materials, plastics, silicon, quartz (fused silica), borosilicate glass (e.g., BOROFLOAT® borosilicate glass), sapphire, plastic materials.

At a site formation phase 830, reaction sites 832 (or individual sites) are formed on the passivation layer. The reaction sites 832 may be located on the passivation layer so that each of the reaction sites 832 is located with respect to an associated light detector (not shown in FIG. 17), such as the light detector 436. More specifically, a reaction site 832 is located relative to the associated light detector such that a substantial portion of light emissions that propagate toward the detector surface propagate through the detection path of the associated light detector and/or are incident upon the light detector. A substantial portion of light emissions may be greater than any other portion of light emissions that are detected by other light detectors. In other words, a substantial portion is greater than crosstalk portions detected by non-associated light detectors.

A range of different techniques are presently contemplated for formation of the individual sites. One of these techniques is adapted to dispose a material at each site location that can be built upon for accommodating the molecule capture and amplification desired. Exemplary techniques include nano-imprint lithography, described in greater detail below, as well as dip pen lithography, photolithography, and micelle lithography. In one presently contemplated embodiment, the reaction sites are formed by deposition of a base pad at each site location. The site pads may be made of any suitable material, such as gold or another metal. Other suitable material may include silanes, functional biomolecules such as avidin or functionalized organic or inorganic molecules, titanium, nickel, and copper. Alternatively, the site pads can be created by simply blocking the interstitial space with a resist or chemical moiety that resists attachment of a binding moiety leaving the site pad composed of native substrate material (i.e. glass, etc). The site pads can then be derivatized with binding moieties that react specifically with the substrate material (i.e. glass, etc.) and not interstitial space. It should be noted that the array of base pads could be an array of nanodots or nanoparticles.

Once the sites are laid out on the passivation layer, site preparation may proceed as indicated at reference numeral 834, resulting in a prepared microarray 836 ready to be further processed to receive a sample of molecules to be tested. This phase of the manufacturing process may include deposition of various materials on the pads, but also around the pads or over the entire extent of the passivation layer. These materials can be adapted to enhance the capture of a single molecule at each site location, and optionally for subsequently amplifying the molecules for further reading analysis.

It should also be noted that while biosensors have a single prepared functionalized surface as illustrated and described here, the biosensors may be used in applications where more than one functionalized surface is prepared and used for molecule captures, amplification, reading and analysis. In some embodiments, the biosensors are configured to receive solutions in the flow channel that permits the introduction of chemistry useful for adding nucleotides and other substances, templates for reading, sequencing, and so forth, agents for deblocking locations on the templates, washing and flushing liquids, and so forth. For example, U.S. patent application publication no. US 2010/0111768 A1 and U.S. Ser. No. 13/273,666, each of which is hereby incorporated by reference in its entirety, describe similar protocols for flow cells. These protocols may also be used with the biosensors described herein.

Figure 17:
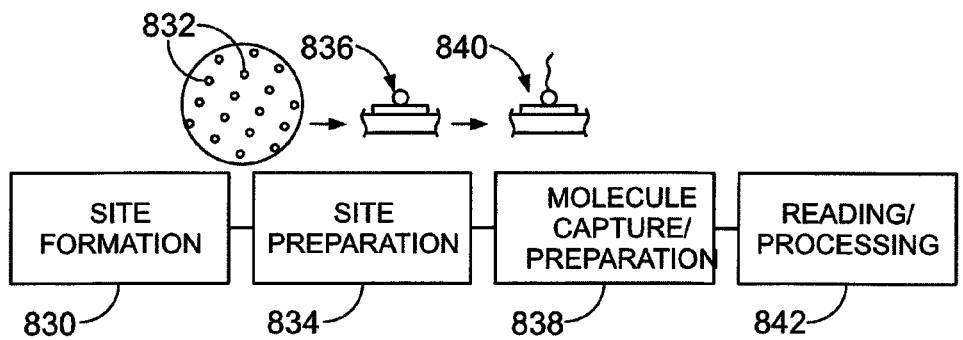
FIG. 17 is a diagrammatical representation of general phases in patterning a detector surface of an exemplary biosensor.

Once the functionalized surface has been prepared and the flow cell has been mounted to the detection device, the biosensor can be employed to capture a single molecule at each site location as indicated by the molecule/capture phase 838 in FIG. 17. This single molecule will typically be amplified, such as by bridge amplification, although other amplification processes may also be used. For example, amplification of a template nucleic acid can be carried out using bridge amplification as described in U.S. Pat. No. 5,641,658 or 7,115,400; or in U.S. Pat. Pub. Nos. 2002/0055100 A1, 2004/0096853 A1, 2004/0002090 A1, 2007/0128624 A1, or 2008/0009420 A1, each of which is incorporated herein by reference in its entirety. In this example, the bridge amplification can be primed by primer nucleic acids that are attached to a porous attachment layer that is in contact with a base pad to which a template nucleic acid is attached. Thus, the base pad can seed growth of a cluster of nucleic acid copies of the template that forms in the porous attachment layer around the base pad.

Another useful method for amplifying nucleic acids is rolling circle amplification (RCA). RCA can be carried out, for example, as described in Lizardi et al., *Nat. Genet.* 19:225-232 (1998) or US Pat. Pub. No. 2007/0099208 A1, each of which is incorporated herein by reference in its entirety. Also useful is multiple displacement amplification (MDA), for example, using a product of RCA (i.e. an RCA amplicon) as a template. Exemplary methods of MDA are described in U.S. Pat. Nos. 6,124,120; 5,871,921; or EP 0,868,530 B1, each of which is incorporated herein by reference in its entirety. In embodiments that include an amplification step, one or more primers that are used for amplification may be attached to a base pad or the porous attachment layer. The primers need not be attached to a base pad or a porous attachment layer in some embodiments.

A single molecule that is captured at a reaction site or otherwise used in a method or composition herein can be a nucleic acid that is single stranded or double stranded. Typically the nucleic acid will have a single copy of a target sequence of interest. Nucleic acids having concatameric copies of a particular sequence can be used (e.g. products of rolling circle amplification). However, in many embodiments the nucleic acid will not have concatameric copies of a sequence that is at least 100 nucleotides long or that is otherwise considered a target sequence for a particular application of the methods. Although the methods and compositions are exemplified with respect to capture of a single nucleic acid molecule, it will be understood that other molecules and materials such as those set forth above can also be captured at a reaction site or otherwise used.

The prepared functionalized surface with the probes attached, as indicated by reference numeral 840, may then be used for analysis purposes. The reading/processing phase 842 is intended to include the imaging of the reaction sites on the functionalized surface, the use of the image data for analysis of the molecules captured and amplified at each of the reaction sites, and so forth.

As mentioned above, one presently contemplated approach for forming the base pads or site locations on substrate involves large-area patterning of very small features using techniques such as nanoscale imprint lithography. FIGS. 18-23 illustrate exemplary steps in an imprint lithography process. The lithography process may be performed using the passivation layer (or other layers) as the passivation layer is on the detection device 404. Alternatively, the lithography process may be used to manufacture a layer (or layers) that is then subsequently mounted to the detection device.

Figure 18:
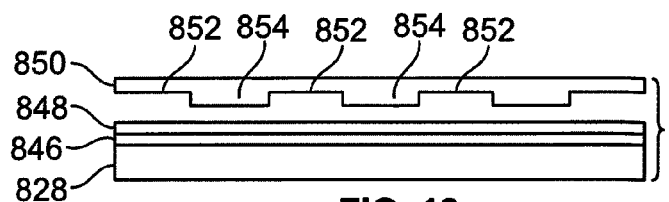
FIGS. 18-23 are diagrammatical representations of successive steps in the disposition of sites on a detector surface of an exemplary biosensor.

Referring first to FIG. 18, a substrate die 828 is first coated with a transfer layer 846, such as by spin or spray coating. In some embodiments, the substrate die 828 may be mounted onto the filter layer 433, which may be mounted onto the substrate layers 432, 431. This layer may be formed of a commercially available resist, such as chlorobenzene and a methylacrylate polymer, and may have a nominal thickness of approximately 70 nm. On this transfer layer, an ultraviolet (UV) imprint resist layer 848 is disposed. The resist layer also may be formed by a polymer which may be spin or spray coated on the transfer layer. This UV imprint resisted layer will form an etch barrier in subsequent processing. This layer may be formed, for example, of tert-butyl methylacrylate and polyester modified polydimethylsiloxane and polyester acrylate and a photo-initiator, at a nominal thickness of approximately 10 nm thicker than the feature height on a working mold 850, typically 70 nm. The working mold 850 is formed in advance, and may be made of various materials, such as glass or modified polydimethylsiloxane. The working mold will be generally transparent to UV light, to permit curing as described below. The desired pattern for the site pad will be formed in the working mold, such that recesses 852 will separate lands 854. The recesses 852 will generally correspond to spaces that will be formed around the pads on the substrate, while the lands 854 in this embodiment will generally correspond to the locations of the pads. The size of the separated lands can be tuned and can range, for example, from 5 nm (nanometers) to 3 µm (micrometers).

Figure 19:
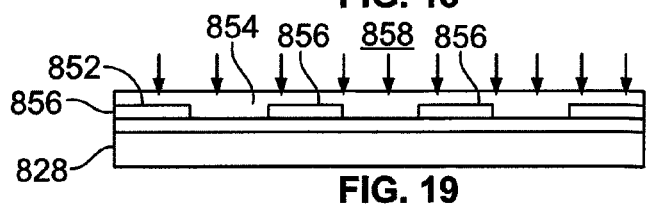
Figure 20:
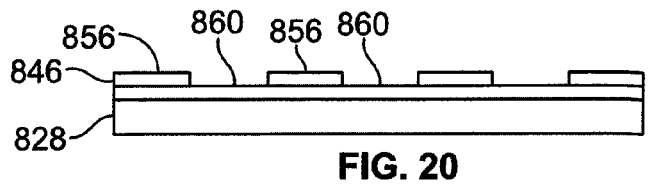
Figure 21:
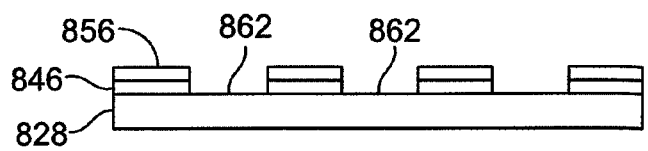
Figure 22:
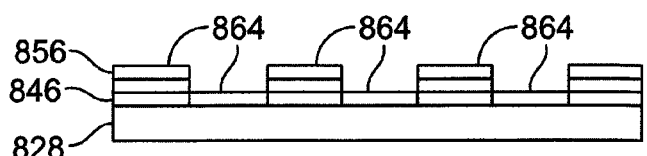
Figure 23:
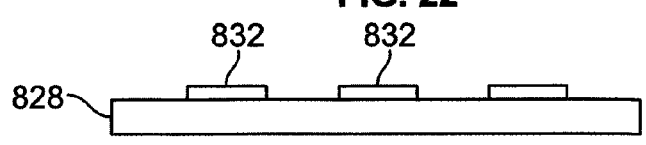

As illustrated in FIG. 19, during processing the mold is brought into contact with the UV imprint layer and displaces portions of this layer to form regions 856 within the recesses 852 of the mold. That is, the lands 854 displace the UV imprint resist layer such that the lands are generally adjacent to the underlying transfer layer. With the mold in place, then, the structure is exposed to UV radiation to at least partially cure the regions 856, rendering them resistant to subsequent etching and effectively transferring the pattern on the working mold into the resist. With the mold then removed, as illustrated in FIG. 20, the transfer layer 846 remains on the substrate die 828, and the remaining regions 856 of the UV imprint resist layer remain to protect the underlying regions of the transfer layer. Exposed transfer regions 860 remain at what will become the locations of the site pads. An etch process is then used to remove these regions as illustrated in FIG. 21. Once the exposed transfer regions are removed, exposed substrate regions 862 will remain. Subsequently, the structure is subjected to a deposition process, such as a metal deposition, to deposit a layer of material 864 over both the regions 856 and the exposed substrate regions 862. In a currently contemplated embodiment, the deposition is of a thin layer of gold, although other materials may include Al, $Al_2O_3$, Zn, ZnO, Ni, Ti, $TiO_2$, ITO (Indium tin oxide), etc. Moreover, the deposition may be to any desired thickness, such as a nominal thickness of 5 nm. Finally, in a lift-off step, the layers above and below the regions 856, including these regions themselves are removed to leave only the pads at locations 832 and the substrate die 828. This lift-off operation may involve solvent washing steps and sonification. Following these processes, a substrate die 828 will be provided with the sites determined and formed in the desired pattern of sites, domains, regions, and so forth. The substrate die 828 may be the passivation layer 434 described herein with respect to the detection device 404. The pads may become part of the reaction sites 414.

Figure 24:
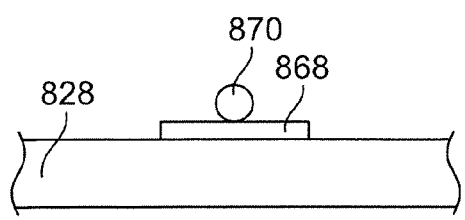
FIGS. 24-26 are diagrammatical representations of steps in the preparation of reaction sites.

Once the sites are laid out and formed by positioning the site pads on the substrate, subsequent building of the sites and preparation steps may take place. As illustrated in FIG. 24, in a presently contemplated embodiment, each base pad 868 receives a capture substance 870 designed to promote the capture of a single molecule of interest. FIG. 24, as with other figures in this disclosure, is not necessarily drawn to scale. For example, the capture substance can be submicroscopic in size (e.g. a linker molecule) or can be a particle that is, at least in some cases, visible under a microscope. In a presently contemplated embodiment, the substance comprises thio-avidin, although other substances may be utilized, such as silanes, biotin-binding proteins, functional biomolecules such as avidin, streptavidin, neutravidin, and functionalized organic or inorganic molecules. An example is a gold-patterned array functionalized with thiol-avidin to bind single molecules modified with biotin. Other capture substances may include, for example, biological binding molecules including neutravidin, streptavidin, antibodies, etc., chemical binding moieties such as amines, aldehydes, carboxyl groups, etc.; and inorganic binding moieties such as metal chelates (i.e. histidine binding), gold (thiol binding), etc.

A capture substance can be attached to a base pad or site via a covalent or non-covalent linkage. Exemplary covalent linkages include, for example, those that result from the use of click chemistry techniques. Exemplary non-covalent linkages include, but are not limited to, non-specific interactions (e.g. hydrogen bonding, ionic bonding, van der Waals interactions etc.) or specific interactions (e.g. affinity interactions, receptor-ligand interactions, antibody-epitope interactions, avidin-biotin interactions, streptavidin-biotin interactions, lectin-carbohydrate interactions, etc.). Exemplary linkages are set forth in U.S. Pat. Nos. 6,737,236; 7,259,258; 7,375,234 and 7,427,678; and US Pat. Pub. No. 2011/0059865 A1, each of which is incorporated herein by reference.

Figure 25:
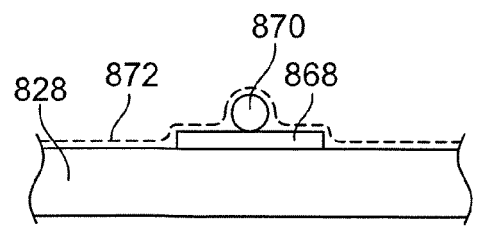
Figure 26:
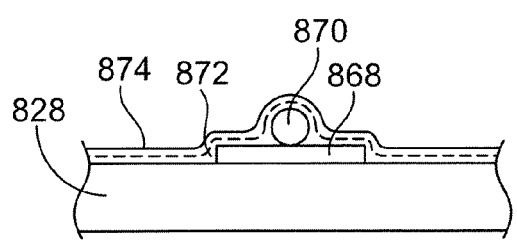

As illustrated in FIG. 25, then, in a presently contemplated embodiment a charged layer 872 may be disposed over the pads and capture substance. In this embodiment, if used, the charged layer comprises aminopropyltriethoxysilane (APTES). This charged layer may promote the attachment of the single molecules at each site, while preventing attachment where not desired. As illustrated in FIG. 26, an attachment layer 74 is disposed over at least the pads 868, and in the illustrated embodiment may be disposed over the entire substrate. In other embodiments, the attachment layer can be patterned such that it is present over the pads or sites but substantially absent over interstitial regions between the pads or sites.

An attachment layer used in a method or composition herein may be formed of a micro-porous material, such as silane-free acrylamide (SFA). Silane-free acrylamide (SFA) polymer can be formed by polymerization of silane free acrylamide and N—(S bromoacetamidylpentyl) acrylamide (BRAPA). Other attachment layers that can be used include without limitation, acrylamide, methacrylamide, hydroxyethyl methacrylate, N-vinyl pyrrolidinone or derivatives thereof. Such materials are useful for preparing hydrogels. In some embodiments, the polymerizable material can include two or more different species of compound that form a co-polymer. Exemplary hydrogels and polymerizable materials that can be used to form hydrogels are described, for example, in US Pat. Pub. No. 2011/0059865 A1, which is incorporated herein by reference in its entirety. Other hydrogels include but are not limited to, polyacrylamide polymers formed from acrylamide and an acrylic acid or an acrylic acid containing a vinyl group as described, for example, in WO 00/31148 (incorporated herein by reference in its entirety); polyacrylamide polymers formed from monomers that form [2+2] photo-cycloaddition reactions, for example, as described in WO 01/01143 or WO 03/014392 (each of which is incorporated herein by reference in its entirety); or polyacrylamide copolymers described in U.S. Pat. No. 6,465,178, WO 01/62982 or WO 00/53812 (each of which is incorporated herein by reference in its entirety). The attachment layer can function to attach the single molecules and/or it can provide locations for attachment of identical molecules (i.e. copies of the single molecules) at each site during amplification.

As noted above, various layouts may be envisaged for the sites of the microarray. Moreover, the density, location, pitch, and sizes of the sites may vary depending upon such factors as the array design, the type of processing and imaging equipment used for analyzing the arrays, and the molecules to be processed. By way of example, presently contemplated sites made as set forth in the present disclosure may have sizes of approximately 30-300 nm. The sites can be disposed on the substrate in a hexagonal pattern. The sites can be present at a density of approximately 1 million capture sites per square millimeter, but can easily be tuned by adjusting the pitch to densities greater than 5 million capture sites per square millimeter. While the particular pitch of the sites may vary, depending, for example, upon their size and the density desired, typical pitches may include at most about 5 micron, 2 micron 1 micron, 850 nm or an even lower maximum value.

Figure 27:
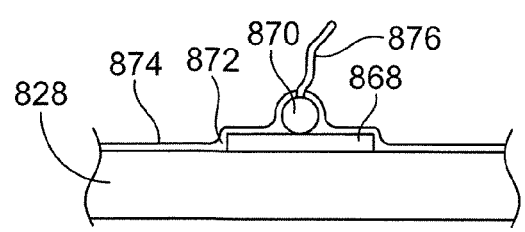
FIGS. 27 and 28 are diagrammatical representations of single nucleic acid molecule capture followed by amplification to create multiple copies of the nucleic acid molecule.
Figure 28:
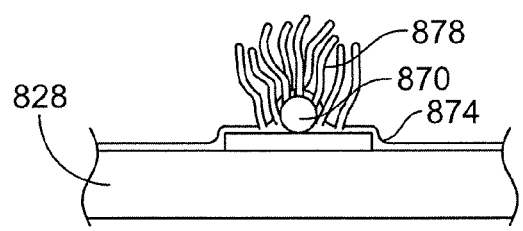

The sites or pads used in various embodiments can be in a size range that is useful for capture of a single nucleic acid template molecule to seed subsequent formation of a homogenous colony, for example, via bridge amplification. FIG. 27 illustrates a base pad 868 that is attached to a capture substance 870 that is in turn attached to a single nucleic acid template 876. The nucleic acid template is illustrated as extending out of the attachment layer 874. However, in some embodiments the nucleic acid template can be retained under or within the volume of the attachment layer. Bridge amplification can be primed by primer nucleic acids that are attached to the attachment layer (e.g. the attachment layer can be a gel) to seed growth of a cluster of nucleic acid copies of the template that forms in or on the attachment layer around the base pad 868.

In an exemplary bridge amplification method, a template nucleic acid hybridizes to a gel-attached primer and the 3' end of the primer is extended to create a complementary copy of the template. In some embodiments two different primers can be attached to the gel. The primers can form a pair used for amplification of a template and its complementary copy. As such, two primers can be used for amplification of the template into multiple copies to form a nucleic acid cluster or population of amplicons. For example, amplification can be carried out using bridge amplification to form nucleic acid clusters attached to the gel. Useful bridge amplification methods are described, for example, in U.S. Pat. Nos. 5,641,658 and 7,115,400; U.S. Pat. Pub. Nos. 2002/0055100 A1, 2004/0096853 A1, 2004/0002090 A1, 2007/0128624 A1, and 2008/0009420 A1, each of which is incorporated herein by reference in its entirety. Other useful methods for amplifying nucleic acids using one or more gel-attached primers are rolling circle amplification (RCA) and multiple displacement amplification (MDA).

In particular embodiments, a cluster of nucleic acids may have a foot print that is no larger than the area of the base pad. For example, the attachment layer 874 may be confined to the foot print of the base pad 868. As such the base pad (and optionally the attachment layer) can form a cluster restriction zone along the lines illustrated in FIG. 28. Alternatively, the foot print of a cluster may be larger than the base pad 868 from which it was seeded.

The incorporated '266 Application also describes various methods of preparing a detector surface having a designated pattern of reaction sites. At least some of these methods may be used to pattern the detector surfaces of the exemplary biosensors described herein. For example, the surface of the passivation layer may have an array of discrete metal regions in which each metal region is surrounded by interstitial region(s), such as glass. The metal regions may be fabricated on the surface of the passivation layer by etching or photolithographic processes. The metal regions may be, for example, aluminum oxide or gold. The metal regions may be used to form the reaction sites having analytes-of-interest as described herein. In particular embodiments, the metal regions have clusters of nucleic acids thereon.

Figure 29:
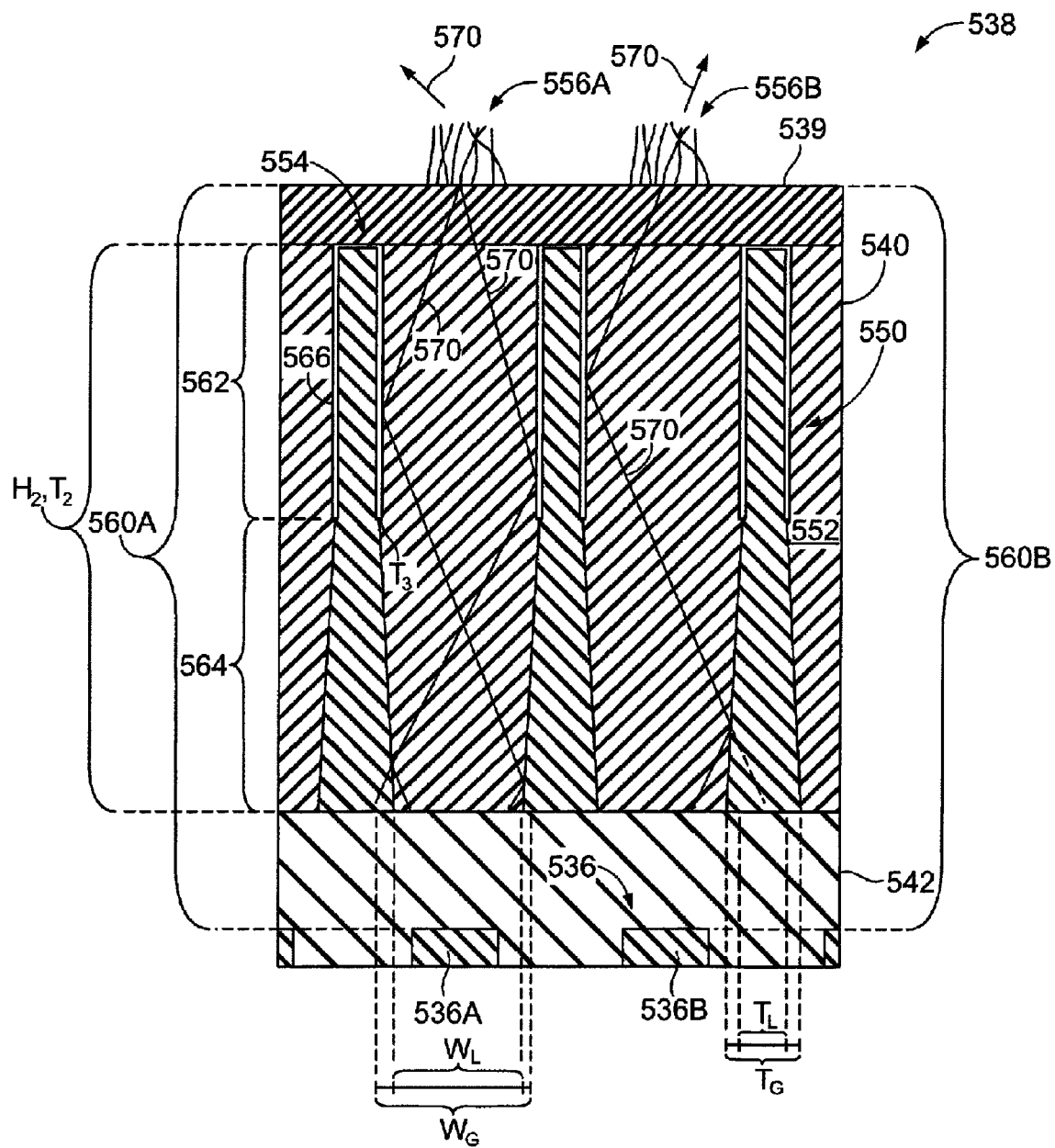
FIG. 29 is an enlarged cross-section of a filter layer that may be used in a biosensor formed in accordance with one embodiment.

FIG. 29 is an enlarged cross-section of a portion of a biosensor 538, which may have similar features as the biosensor 400 (FIG. 7). For example, the biosensor 538 includes a passivation layer 539, a filter layer 540, and a solid-state imager 542 having light detectors 536. Similar to the filter layer 433 (FIG. 7), the filter layer 540 may include filter walls 550 and a light-absorbing material 552 extending between adjacent filter walls 550. In the illustrated embodiment, the filter walls 550 have a height $H_2$ and the light-absorbing material 552 has a thickness $T_2$ that is substantially equal to the $H_2$. However, in alternative embodiments, the thickness $T_2$ may be less than the height $H_2$ such that reaction chambers may be defined, or the thickness $T_2$ may be greater than the height $H_2$ such that ends 554 of the filter walls 550 are located a depth into the light-absorbing material 552.

The filter walls 550 may include first and second interior portions 562 and 564 in which the first interior portion 562 is coated with a coating material 566 and the second interior portion 564 is not coated or is coated with a different material. In the illustrated embodiment, the coating material 566 is a reflective material. In an exemplary embodiment, the first interior portion 562 is coated with a material that includes aluminum or another metal and has a thickness $T_3$ that is, at most, about 3000 A. In some embodiments, the thickness $T_3$ of the coating material 566 is less than about 2000 A or less than about 1000 A. In more particular embodiments, the coating material 566 has a thickness $T_3$ that is less than about 600 A. In some embodiments, the thickness $T_3$ of the coating material 566 tapers or decreases as the coating material 566 extends closer to the solid-state imager 542. For example, the thickness $T_3$ may be about 600 A near an end 554 of the filter wall 550 that is proximate to the passivation layer 539. However, the thickness $T_3$ may decrease to zero as the coating material 566 extends toward the solid-state imager 542.

As shown, a detection path 560A extends between the reaction site 556A and the light detector 536A, and another detection path 560B extends between the reaction site 556B and the light detector 536B. A detection path represents the general space or volume of the biosensor 538 that light (e.g., emission light, excitation light, and crosstalk light) propagates through from one reaction site 556 to an associated light detector 536. The detection paths 560A, 560B extend through the passivation layer 539, the filter layer 540, and a portion of the material in the solid-state imager 542.

In FIG. 29, the reaction sites 556A, 556B may be characterized as being adjacent to each other. Likewise, the light detectors 536A, 536B may be characterized as being adjacent to each other. Also, the light detector 536A is positioned with respect to the filter walls 550 and the reaction site 556A to detect emission light from the reaction site 556A. As such, the light detector 536A and the reaction site 556A are characterized as being associated with each other. Similarly, the light detector 536B and the reaction site 556B are characterized as being associated with each other because the light detector 536B is configured to detect emission light from the reaction site 556B.

Also shown in FIG. 29, the detection paths 560 may have a changing or reducing width. The width for each of the detection paths 560 may begin to decrease at some point as the detection path 560 extends toward the solid-state imager 542. For example, the filter walls 550 may have an increasing thickness as the filter walls 550 extend from the ends 554 toward the solid-state imager 542. For example, the ends 554 may have a thickness TL that is between about 0.4 microns to about 1.2 microns. In particular embodiments, the thickness TL is about 0.8 microns at the ends 554. As shown in FIG. 29, the thickness TL may begin to increase as the filter wall 550 transitions from the first interior portion 562 to the second interior portion 564. The filter walls 550 may have a thickness TG at the solid-state imager 542. Consequently, as the thickness increases, the width decreases from WG to about WL. In the illustrated embodiment, the light detectors 536 have a width WD that is about equal to 1.4 microns. However, the light detectors 536 may be less than or more than 1.4 microns in other embodiments.

Example light rays 570 that are emitted from the reaction sites 556 are shown in FIG. 29. Light emissions may propagate from the reaction site 556 or, more specifically, from the analyte-of-interest from the reaction site 556 in an isotropic manner. Accordingly, at least some of the light rays 570 are transmitted through the detection paths 560A, 560B toward the light detectors 536. As shown in FIG. 29, the light rays 570 that are reflected by the coating 566 may be less attenuated than the light rays 570 that are reflected by the second interior portion 564 of the filter walls 550. In such embodiments, quantum efficiency (QE) of the light detected by the light detectors 536 may be improved.

Figure 30:
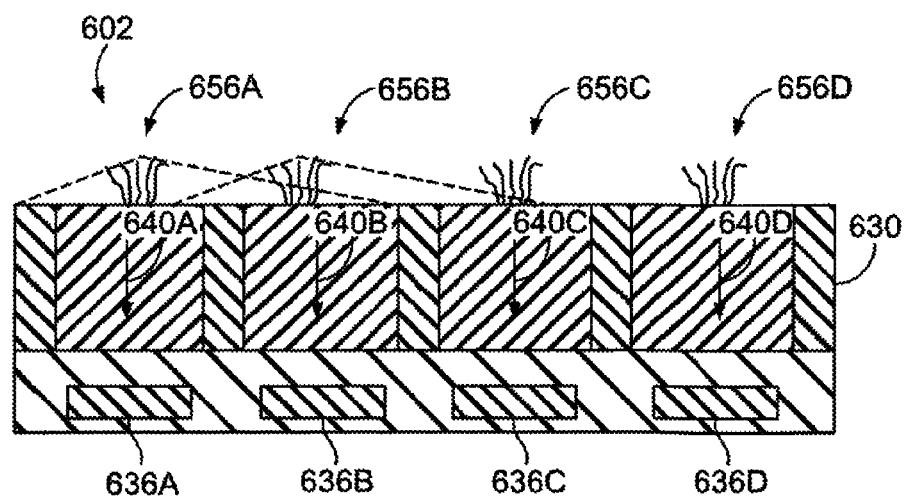
FIG. 30 illustrates an exemplary detection device for biological and/or chemical analysis formed in accordance with one embodiment.

FIG. 30 illustrates a detection device 600 having a plurality of reaction sites 656A-656D on a detector surface 602. The detection device 600 includes light detectors 636A-636D and may be similar to other detection devices described herein. The light detectors 636A-636D are associated with the reaction sites 656A-656D, respectively. Corresponding detection paths 640A-640D extend between the light detectors 636A-636D and corresponding reaction sites 656A-656D. The arrows that indicate the detection paths 640A-640D are merely to illustrate a general direction that the light propagates through the respective detection path.

During an imaging event, the detection device 600 is configured to detect light using the light detectors 636A-636D. As demonstrated in FIG. 30 by pyramidal hash marked areas or zones, light emissions (or emission signals) are propagating from the reaction sites 656A and 656B, but light emissions are not propagating from 656C or 656D. The light emissions may be indicative of, for example, a positive binding event between the analytes-of-interest located at the corresponding reaction site and another biomolecule. In particular embodiments, the reaction sites 656A-656D are illuminated by an excitation light (e.g., 532 nm). The reaction sites 656A and 656B are bound to respective biomolecules having light labels (e.g., fluorescent moieties). In response to the excitation stimulus, the reaction sites 656A and 656B provide light emissions as demonstrated in FIG. 30.

However, the reaction sites 656 and the light detectors 636 may be located relatively close to one another such that light emissions from a non-associated reaction site may be detected by a light detector. Such light emissions may be referred to as crosstalk emissions. By way of example, the light emissions propagating from the reaction site 656A include a crosstalk portion and a site portion. The site portion of the light emissions from the reaction site 656A is that portion of the light emissions that is configured to be detected by the light detector 636A. In other words, the site portion includes the light emissions that propagate at an angle that is generally toward the light detector 636A such that filter walls 630 defining the detection path 640A are capable of directing the light emissions toward the light detector 636A. The crosstalk portion is that portion of the light emissions that clears the filter walls 630 defining the detection path 640A and propagates into, for example, the detection path 640B. In such cases, the crosstalk portion may be directed to the light detector 636B, which is not associated with the reaction site 656A. Thus, the light detector 636B may be referred to as a non-associated light detector with respect to the reaction site 656A.

Using the embodiment shown in FIG. 30 as an example, the light detector 636A may detect the site emissions from the reaction site 656A and the crosstalk emissions from the reaction site 656B. Likewise, the light detector 636B may detect the site emissions from the reaction site 656B and the crosstalk emissions from the reaction site 656A. The light detector 636C may detect the crosstalk emissions from the reaction site 656B. However, the reaction site 656C is not providing light emissions in FIG. 30. Thus, an amount of light detected by the light detector 636C is less than the corresponding amounts of light detected by the light detectors 636A and 636B. As shown in FIG. 30, the light detector 636C only detects crosstalk emissions from the reaction site 656B, and the light detector 636D does not detect crosstalk emissions or site emissions.

Figure 31:
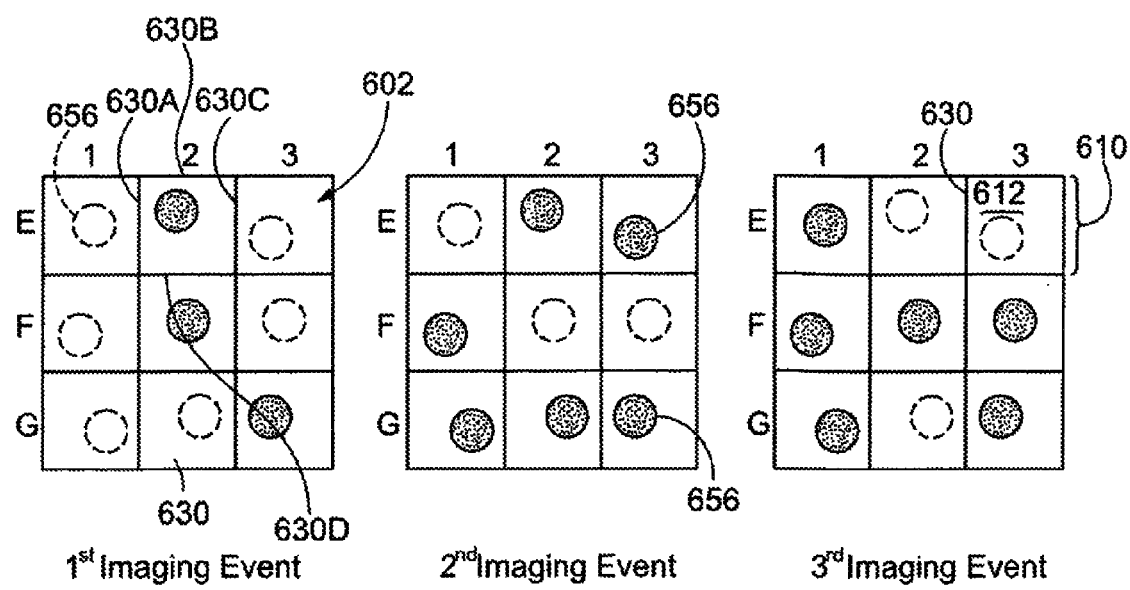
FIG. 31 is a top plan view of an exemplary detector surface during first, second, and third imaging events in accordance with one embodiment.

FIG. 31 is a top plan view of the detector surface 602 during first, second, and third imaging events. The detector surface 602 includes a set of the reaction sites 656. The reaction sites 656 are labeled by row-letter and column-number. In the illustrated embodiment, the reaction sites 656 remain in the same position or location for the multiple imaging events. The detector surface 602 may include a plurality of image areas 610 that are defined by the filter walls 630. In FIG. 31, the image areas 610 are substantially square-shaped, but other shapes may be implemented. In the illustrated embodiment, each of the image areas 610 includes only a single reaction site 656 that covers a site area 612. The site area 612 may be substantially circular as shown in FIG. 31 or may have other shapes. Furthermore, the site areas 612 are not required to have the same or similar shapes. In FIG. 31, the site area 612 is substantially less than the corresponding image areas 610. However, in other embodiments, the site area 612 may be slightly less than, substantially equal to, or slightly greater than the corresponding image area 610. In such embodiments in which the site area 612 is greater than the image area 610, adjacent image areas 610 may be separated by greater distances to accommodate the site areas 612. For example, the filter walls 630 may be configured to be thicker. Alternatively, the detector surface 602 may be configured so that inactive image areas 610 that do not have a corresponding reaction site 656 separate active image areas 610 that do have a reaction site 656.

In some embodiments, the reaction sites 656 may not have a common location with respect to the filter walls 630 that define the detection path. This may be due to, for example, tolerances in the manufacturing or sample preparation processes. For example, as shown in FIG. 31, the reaction site 656 at E1 is substantially centered between four filter walls 630, but the reaction site 656 at E2 is closer to walls 630A and 630B than walls 630C and 630D. During different imaging events, a different number of reaction sites may emit light that is indicative of a desired reaction (e.g., binding event). In FIG. 31, the darker-shaded reaction sites 656 (or site areas 612) indicate that the reaction site 656 is providing emission signals during the corresponding imaging event, and the non-shaded and hashed reaction sites 656 (or site areas 612) indicate that the reaction site 656 is not providing emission signals during the imaging event. For instance, the reaction sites E2, F2, and G3 are emitting light during the first imaging event; the reaction sites E2, E3, F1, G1, G2, and G3 are emitting light during the second imaging event; and the reaction sites E1, F1, F2, F3, G1, and G3 are emitting light during the third imaging event.

Embodiments described herein may be configured to account for crosstalk emissions from adjacent reaction sites when analyzing signal data from the detection device. For example, each light detector 636 (FIG. 30) may be assigned a crosstalk function that is based on whether adjacent reaction sites are providing light emissions. In some cases, the crosstalk function may be based on an amount of light emitted from the adjacent site(s), which may be determined by an amount of light detected by the light detector(s) that is/are associated with the adjacent site(s). For example, the reaction site 656 at F1 during the third imaging event is providing emission signals and the reaction sites at E1, F2, and G1 are also providing emission signals. Thus, a substantial portion of an amount of light detected by the light detector associated with the reaction site 656 at F1 may be due to crosstalk emissions from the reaction sites at E1, F2, and G1.

As another example, the reaction site 656 at F2 during the second imaging event does not provide light emissions. However, six adjacent reaction sites 656 (E2, E3, F1, G1, G2, and G3) may provide crosstalk emissions. Thus, during the second imaging event, an entire portion of light detected by the light detector associated with the reaction site 656 at F2 is due to crosstalk emissions from the reaction sites 656 at E3, E3, F1, G1, G2, and G3. The cumulative effect of the crosstalk emissions from the reaction sites 656 at E2, E3, F1, G1, G2, and G3 may result in an incorrect determination as to whether a binding event occurred at the reaction site of F2.

Figures 32, 33:
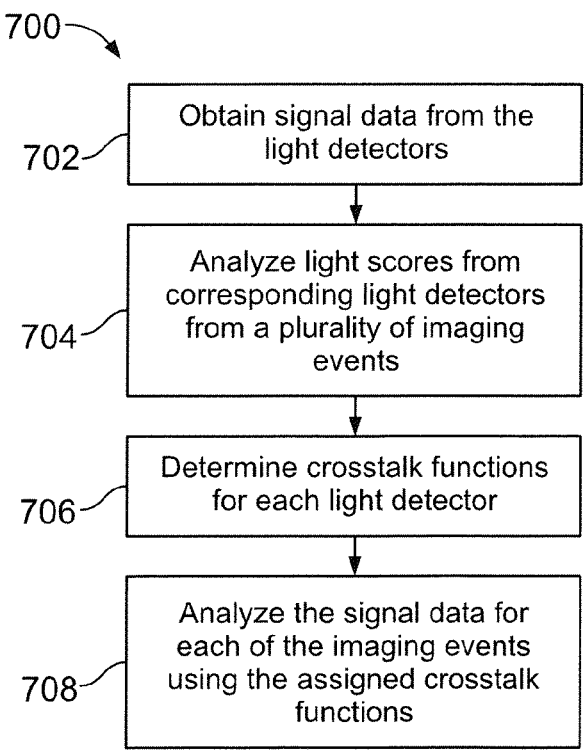
FIG. 32 illustrates light scores or values obtained by light detectors in an exemplary detection device in accordance with one embodiment.
FIG. 33 shows an exemplary method of analyzing signal data obtained from a detection device used for biological and/or chemical analysis.

FIG. 32 illustrates exemplary light scores or values obtained by the light detectors that are associated with the reaction sites 656 shown in FIG. 31. In the illustrated embodiment, the light scores range from 5-105. However, these are only illustrative and other ranges may be used or other manners for indicating a light score. As shown, light scores obtained by light detectors may be substantially based upon non-associated reaction sites as well as the associated reaction sites. For example, the light score for F2 during the second imaging event is 60 even though the reaction site 656 at F2 did not provide emission signals. During the third imaging event, both of the reaction sites 656 at F2 and G3 provide emission signals, but the light score associated with the reaction site 656 at F2 is greater than the light score associated with the reaction site 656 at G3 due to crosstalk emissions.

FIG. 33 shows a method of 700 analyzing signal data obtained from a detection device, such as the detection devices described above. The method may be used to analyze light emissions (or emission signals) from reaction sites that have a fixed position with respect to the associated light detectors of the detection device and that are exposed to a stimulus (e.g., excitation light) multiple times (i.e., for separate imaging events). The method 700 may be performed by, for example, the analysis module 138 (FIG. 2). The method 700 may include obtaining at 702 signal data from the light detectors. The signal data may include light scores, such as those shown in FIG. 32, that are based on an amount of light detected by the light detectors during an imaging event. The amount of light detected by the light detectors may include site emissions and crosstalk emissions. More specifically, the amount of light detected by one light detector may be based on whether crosstalk emissions from non-associated reaction site(s) are also detected by the corresponding light detector. The amount of light detected by the light detector may also depend upon other factors, such as excitation light, manufacturing tolerances, electrical noise in the detection device, etc.

The method 700 also includes analyzing at 704 the light scores from a set or group of light detectors from a plurality of the imaging events to determine at 706 respective crosstalk functions of the light detectors. The group of light detectors may be an array or sub-array of a detection device. The group of light detectors may be proximate to one another (e.g., one light detector may be adjacent to or within the immediate vicinity of other light detectors). For instance, the group of light detectors may be the light detectors associated with the reaction sites 656 shown in FIG. 31.

In some embodiments, the crosstalk function may be determined by analyzing a relationship between a light score that is associated with one reaction site (i.e., site-of-interest) and the light scores that are associated with adjacent reaction sites. For example, it may be assumed that a light score of the reaction site 656 at G2 is dependent upon whether the reaction site 656 at G2 provided light emissions (i.e., site emissions) and whether the adjacent reaction sites 656 at F1, F2, F3, G1, and G3 also provided light emissions (i.e., crosstalk emissions). More specifically, the light score may be based on (a) the site emissions from the reaction site 656 at G2 (if any) and (b) the crosstalk emissions from the adjacent reaction sites 656 at F1, F2, F3, G1, and G3. By way of example, during the first imaging event, the reaction site 656 at G2 has a light score of 15. The reaction site 656 at G2 did not provide light emissions, which may indicate that a binding event did not occur at the G2 prior to or during the imaging event. Thus, the value of the light score is based on the crosstalk portions from the adjacent reaction sites 656 at F1, F2, F3, G1, and G3 that actually provided light emissions. Whether or not a reaction site provides light emissions can be determined by identifying whether the reaction site in question had a light score that exceeded a designated value (e.g., 70). In this example, the reaction sites 656 at F2 and G3 provide light emissions during the first imaging event. Other methods may be used to determine whether a reaction site provides light emissions.

However, the reaction site 656 at G2 during the third imaging event received a light score of 40. Like the first imaging event, both of the reaction sites 656 at F2 and G3 provide light emissions. However, unlike the first imaging event, the reaction sites 656 at F1, F3, and G1 also provide light emissions. Thus, it may be assumed that the difference between the light scores of the first and third imaging events (i.e., 15 and 40) for the reaction site 656 at G2 may be based on the crosstalk portions from the reaction sites 656 at F1, F3, and G1. By analyzing the light scores of the light detectors in a similar manner for multiple imaging events, a crosstalk function for each of the light detectors may be determined. In some embodiments, the crosstalk function is determined by a total number of adjacent reaction sites that provide emissions signals. For example, for each adjacent reaction site that provides emission signals (e.g., had a light score of 70 or greater), a predetermined value may be added to the crosstalk function for the site-of-interest. In some embodiments, the crosstalk function may be based not only on the number of adjacent reaction sites, but also the particular combination of adjacent reaction sites. In this other embodiment, the crosstalk function may be affected by the location of the adjacent reaction site(s).

After determining the crosstalk functions, the method 700 may also include analyzing at 708 the signal data for each of the imaging events using the assigned crosstalk functions to determine characteristics of the analytes-of-interest. For instance, the crosstalk function of one light detector may be subtracted from the light score of that light detector to determine a light score that is based primarily on a site emissions (if any). As one example, if a light detector has a light score of 100, but the crosstalk function finds that 30 of the 100 are due to adjacent reaction sites, then the modified (or more accurate) light score is 70. The modified light score may then be used to determine a characteristic of the analyte-of-interest located at the corresponding reaction site.

In one specific application, the characteristic of the analyte-of-interest that is determined is the nucleotide that was recently incorporated into a sequence at the reaction site.

Figure 34:
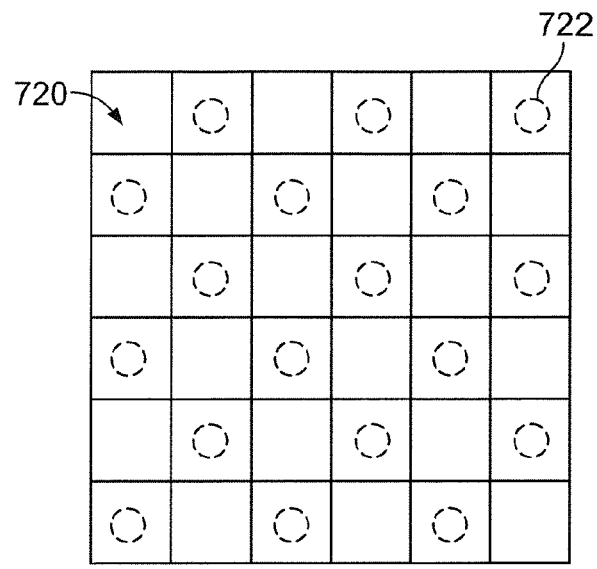
FIG. 34 is a top plan view of an exemplary detector surface having a plurality of reaction sites in accordance with one embodiment.

FIG. 34 is a top plan view of a detector surface 720 having a plurality of reaction sites 722. As shown, in some embodiments, the reaction sites 722 may be positioned with respect to each other to reduce any effect that crosstalk emissions may have on light detection. For instance, at least portions or areas of the detector surface 722 may be unused so that distances between adjacent reaction sites become greater. These may be the inactive image areas described herein. As one example, the pattern or configuration of the reaction sites 722 along the detector surface 720 in FIG. 34 is a "checkerboard" type configuration. In such embodiments, each reaction site is adjacent to, at most, four other reaction sites. However, the checkerboard configuration is only one example and other configuration may be used to control or reduce the effects of crosstalk.

Figure 35:
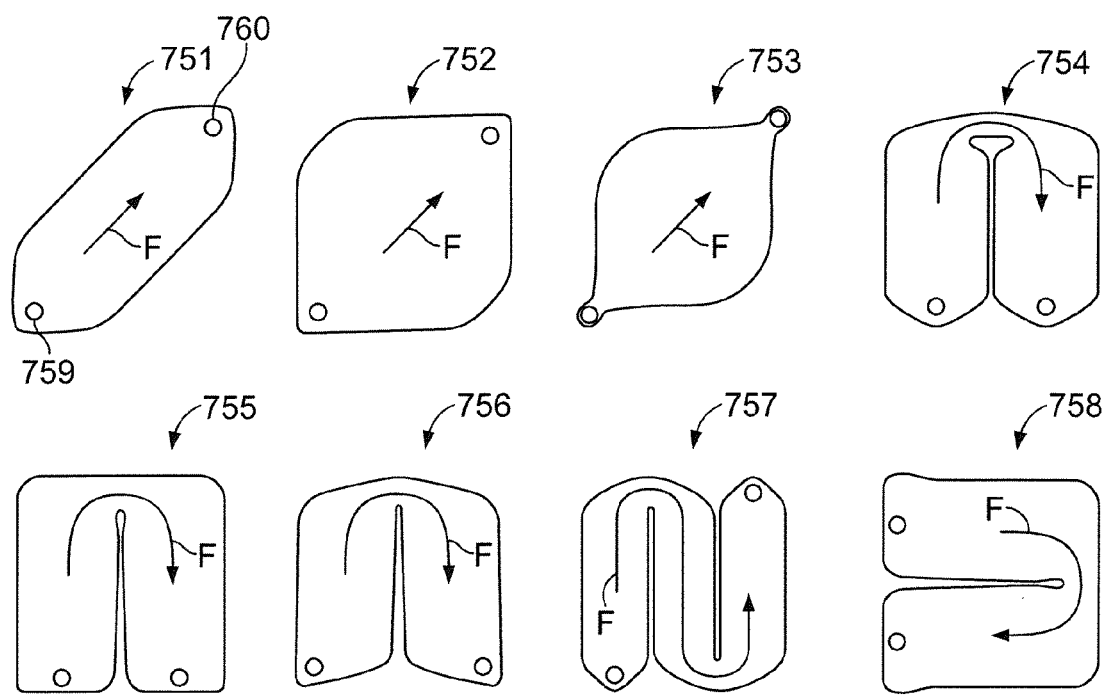
FIG. 35 shows plan views of various configurations of flow cells that may be used with one or more embodiments.

FIG. 35 illustrates a plan view of a variety of exemplary flow cell configurations 751-758 that may be used with one or more embodiments. An inlet port 759 and an outlet port 760 are indicated as circles in the flow cells 751-758. Flow of solution is indicated by arrows labeled F. Embodiments described herein may use flow cells that are sized and shaped to be suitable for an intended purpose. For example, the flow cells may be configured to control flow of the solutions that are moved along the detector surface of the detection device. Controlling flow of a solution may also include controlling bubble formation and bubble disposal. As shown, the flow cells 751-753 may have a single large active area such that the flow of solution does not turn, curve, or bend between the ports 759, 760. However, the flow cells 754-758 may have at least one bend where a direction of flow is curved.

Embodiments described herein may also be used with various detection protocols. For example, U.S. Provisional Application No. 61/538,294, filed Sep. 23, 2011, which is incorporated by reference in its entirety, describes methods and systems that utilize fewer detection moieties than the number of analytes targeted for detection. For example, for detecting the incorporation of four analytes (e.g., during a sequencing reaction) each of the analytes can be differentially labeled and detected by one of four excitation/emission filters (e.g., fluorescent sequencing). Alternatively, methods and systems can also be utilized wherein one dye, or a plurality of dyes with similar detection characteristics, are used when detecting and differentiating multiple different analytes. As such, the number of detection moieties utilized is less than the number of analytes being detected which can also serve to reduce the number of imaging events needed to determine the presence of the different analytes. U.S. application Ser. No. 13/624,200, which was filed on Sep. 21, 2012, is also incorporated by reference in its entirety.

Figure 36:
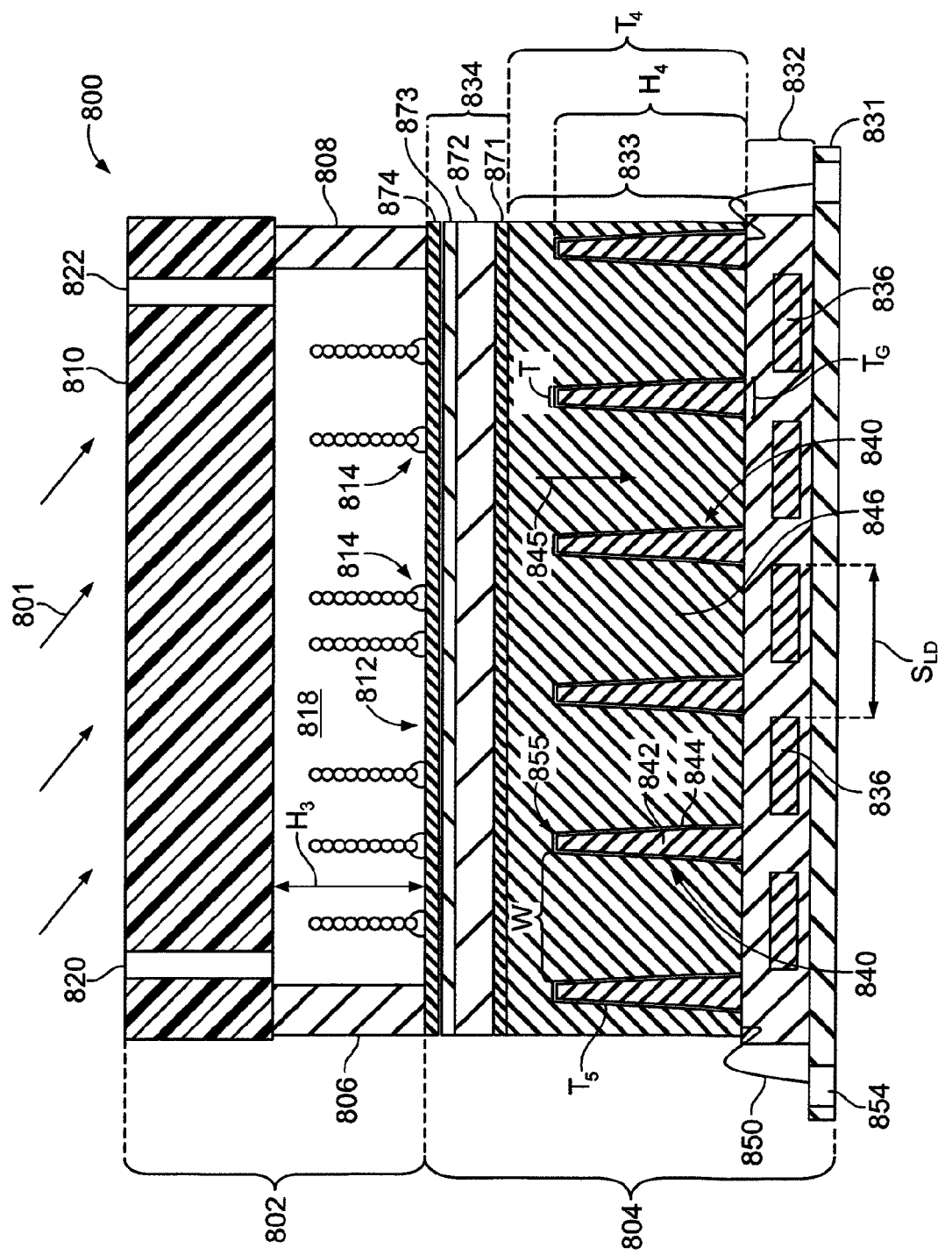
FIG. 36 illustrates a cross-section of an exemplary biosensor formed in accordance with one embodiment.

FIG. 36 illustrates a cross-section of a biosensor 800 formed in accordance with one embodiment. The biosensor 800 may have similar features as the biosensor 102 (FIG. 1) and the biosensor 400 (FIG. 7) described above and may be used in, for example, the cartridge 302 (FIG. 4). As shown, the biosensor 800 may include a flow cell 802 that is mounted onto a detection device 804. In the illustrated embodiment, the flow cell 802 is affixed directly to the detection device 804. However, as described in other embodiments, the flow cell 802 may be removably coupled to the detection device 804. The detection device 804 has a detector surface 812 that may be functionalized (e.g., chemically or physically modified in a suitable manner for conducting the desired reactions). For example, the detector surface 812 may be functionalized and may include a plurality of reaction sites 814 having one or more biomolecules immobilized thereto. In particular embodiments, the reaction sites 814 include clusters or colonies of biomolecules (e.g., oligonucleotides) that are immobilized on the detector surface 812. Such reaction sites may be particularly suitable for SBS sequencing.

In particular embodiments, the detector surface 812 is prepared or modified as described in U.S. application Ser. No. 13/784,368, filed Mar. 4, 2013, and entitled "Polymer Coatings," which is incorporated by reference in its entirety.

In the illustrated embodiment, the flow cell 802 includes sidewalls 806, 808 and a flow cover 810 that is supported by the sidewalls 806, 808. The sidewalls 806, 808 are coupled to the detector surface 812 and extend between the flow cell cover 810 and the sidewalls 806, 808. In some embodiments, the sidewalls 806, 808 are formed from a curable adhesive layer that bonds the flow cover 810 to the detection device 804.

The sidewalls 806, 808 are sized and shaped so that a flow channel 818 exists between the flow cell cover 810 and the detection device 804. In some cases, the dimensions and the shape of the flow channel 818 may be configured to control bubble formation. As shown, the flow channel 818 may include a height $H_3$ that is determined by the sidewalls 806, 808. The height $H_3$ may be between about 50-400 μm (microns) or, more particularly, about 80-200 μm. In particular embodiments, the height $H_3$ may be between about 80-120 μm. In the illustrated embodiment, the height $H_3$ is about 100 μm. The flow cover 810 may include a material that is transparent to excitation light 801 propagating from an exterior of the biosensor 800 into the flow channel 818. As shown in FIG. 36, the excitation light 801 approaches the flow cell cover 810 at a non-orthogonal angle. However, this is only for illustrative purposes as the excitation light 801 may approach the flow cover 810 from different angles. In some cases, the excitation light 801 floods the flow channel 818.

Also shown, the flow cell cover 810 may include inlet and outlet ports 820, 822 that are configured to fluidically engage other ports (not shown). For example, the other ports may be from the cartridge 302 (FIG. 4) or the workstation 300 (FIG. 4). The flow channel 818 is sized and shaped to direct a fluid along the detector surface 812. The height $H_3$ and other dimensions of the flow channel 818 may be configured to maintain a substantially even flow of a fluid along the detector surface 812. The dimensions of the flow channel 818 may also be configured to control bubble formation.

As shown in exemplary FIG. 36, the sidewalls 806, 808 and the flow cover 810 are separate components that are coupled to each other. In alternative embodiments, the sidewalls 806, 808 and the flow cell cover 810 may be integrally formed such that the sidewalls 806, 808 and the flow cell cover 810 are formed from a continuous piece of material. By way of example, the flow cell cover 810 (or the flow cell 802) may comprise a transparent material, such as glass or plastic. The flow cell cover 810 may constitute a substantially rectangular block having a planar exterior surface and a planar inner surface that defines the flow channel 818. The block may be mounted onto the sidewalls 806, 808. Alternatively, the flow cell 802 may be etched to define the flow cell cover 810 and the sidewalls 806, 808. For example, a recess may be etched into the transparent material. When the etched material is mounted to the detection device 804, the recess may become the flow channel 818.

The detector surface 812 may be substantially planar as shown in FIG. 36. However, in alternative embodiments, the detector surface 812 may be shaped to define reaction chambers in which each reaction chamber has one or more of the reaction sites 814. The reaction chambers may be defined, for example, by chamber walls that effectively separate the reaction site(s) 814 of one reaction chamber from the reaction site(s) 814 of an adjacent reaction chamber.

The detection device 804 may be similar to, for example, an integrated circuit comprising a plurality of stacked substrate layers 831-834. The substrate layers 831-834 may include a base substrate 831, a solid-state imager 832 (e.g., CMOS image sensor), a filter or light-management layer 833, and a passivation layer 834. It should be noted that the above is only illustrative and that other embodiments may include fewer or additional layers. Moreover, each of the substrate layers 831-834 may include a plurality of sub-layers. For example, the substrate layer 834 includes layers (or sub-layers) 871-874. The detection device 804 may be manufactured using processes that are similar to those used in manufacturing integrated circuits, such as CMOS image sensors and CCDs. For example, the substrate layers 831-834 or portions thereof may be grown, deposited, etched, and the like to form the detection device 804.

The passivation layer 834 is configured to shield the filter layer 833 from the fluidic environment of the flow channel 818. In some cases, the passivation layer 834 is also configured to provide a solid surface (i.e., the detector surface 812) that permits biomolecules or other analytes-of-interest to be immobilized thereon. For example, each of the reaction sites 814 may include a cluster of biomolecules that are immobilized to the detector surface 812. Thus, the passivation layer 834 may be formed from a material that permits the reaction sites 814 to be immobilized thereto. The passivation layer 834 may also comprise a material that is at least transparent to a desired fluorescent light. By way of example, the passivation layer 834 may include silicon nitride ($Si_3N_4$) and/or silica ($SiO_2$). However, other suitable material(s) may be used. In the illustrated embodiment, the passivation layer 834 may be substantially planar. However, in alternative embodiments, the passivation layer 834 may include recesses, such as pits, wells, grooves, and the like. In the illustrated embodiment, the passivation layer 834 has a thickness that is about 150-300 nm and, more particularly, about 175-250 nm.

In particular embodiments, the passivation layer 834 includes the sub-layers 871-874. The sub-layer 871 may be a stress-matching layer that includes silica ($SiO_2$). The stress-matching layer 871 is configured to support the materials deposited thereon and reduce the likelihood of cracking of the passivation layer 834 and/or other layers. The sub-layer 872 may be a protection layer that includes silicon nitride ($Si_3N_4$). The sub-layer 873 may be a chemical-matching layer including silica ($SiO_2$). The chemical-matching layer 873 may be configured to receive a sample-receiving layer 874. The sample-receiving area 874 may be configured to have samples immobilized thereon. By way of example only, the sub-layers 871-873 may have thicknesses of about 25 nm, about 150 nm, and about 25 nm, respectively. Stress of each sub-layer can be adjusted during deposition so that the overall layer has a desired balance to minimize winkling and bulking effects.

The filter layer 833 may include various features that affect the transmission of light. In some embodiments, the filter layer 833 can perform multiple functions. For instance, the filter layer 833 may be configured to (a) filter unwanted light signals, such as light signals from an excitation light source; (b) direct emission signals from the reaction sites 814 toward corresponding light detectors 836 that are configured to detect the emission signals from the reaction sites; or (c) block or prevent detection of unwanted emission signals from adjacent reaction sites. As such, the filter layer 833 may also be referred to as a light-management layer. In the illustrated embodiment, the filter layer 833 has a thickness that is about 1-10 µm and, more particularly, about 3-6 µm. In the illustrated embodiment, the filter layer 833 is about 4.0 µm.

In some embodiments, the filter layer 833 may include a plurality of filter walls 840. The filter walls 840 may be configured to at least one of (a) reflect emission signals or (b) block or prevent unwanted emissions signals from adjacent reaction sites. Adjacent filter walls 840 may define the detection path 845 for the emission signals that are provided by one or more of the reaction sites 814. The detection path 845 extends between the detector surface 812 to a light detector 836. The filter walls 840 may be formed from various kinds of materials. For example, the filter walls 840 may include an internal material 842 (e.g., glass) and an exterior coating 844 that is deposited onto surfaces of the internal material 842. In the illustrated embodiment, the coating 844 includes a reflective metal (e.g., aluminum). In alternative embodiments, the coating 844 may include a dielectric material.

The filter walls 840 may be similar to the filter walls 550 (FIG. 29). For example, the filter walls 840 have a height $H_4$ and a light-absorbing material 846 has a thickness $T_4$ that is greater than the height $H_4$ of the filter walls 840. In an exemplary embodiment, the coating material 844 includes aluminum or another metal and has a thickness $T_5$ that is, at most, about 3000 Angstroms (A) (or 300 nm). In some embodiments, the thickness $T_5$ of the coating material 844 is less than about 2000 A (or 200 nm) or less than about 1000 A (100 nm). In more particular embodiments, the thickness $T_5$ is less than about 600 A (60 nm). In some embodiments, the thickness $T_5$ of the coating material 844 tapers or decreases as the coating material 844 extends closer to the solid-state imager 832. For example, the thickness $T_5$ may be about 600 A near an end 855 of the filter wall 840 that is proximate to the passivation layer 834. However, the thickness $T_5$ may decrease to zero as the coating material 844 extends toward the solid-state imager 832.

Also shown in FIG. 36, the detection paths 845 between adjacent filter walls 840 may have a changing or reducing width W. The width W for each of the detection paths 845 may begin to decrease at some point as the detection path 845 extends toward the solid-state imager 832 between the adjacent filter walls 840. For example, the filter walls 840 may have an increasing thickness as the filter walls 840 extend from the ends 855 toward the solid-state imager 832. For example, the ends 855 may have a thickness $T_L$ that is between about 0.2 microns to about 1.2 microns. In particular embodiments, the thickness $T_L$ may be between about 0.2 microns and about 0.4 microns. The filter walls 840 may have a thickness $T_G$ at the solid-state imager 832. Consequently, as the thickness increases, the width W decreases. In the illustrated embodiment, the light detectors 836 have a center-to-center spacing $S_{LD}$ that is about equal to 1.4 microns. However, the center-to-center spacing $S_{LD}$ between the light detectors 836 may be less than or more than 1.4 microns in other embodiments.

The light-absorbing material 846 may be deposited over, matched to, or under the filter walls 840. The light-absorbing material 846 may include, for example, a material that is configured to absorb the excitation light and permit the fluorescent emissions (i.e., emission light, emission signals) to pass therethrough. In the illustrated embodiment, the light-absorbing material 846 may comprise a resist-based absorption material that is configured to block, for example, 532 nm excitation light. However, other light-absorbing materials 846 may be used. In alternative embodiments, a dichroic filter may be positioned between adjacent filter walls 840. In other alternative embodiments, a dichroic filter layer is located above or below the filter walls 840. For example, the dichroic filter layer may be located between the passivation layer 834 and the filter layer 833.

In alternative embodiments, the filter layer 833 may include an array of microlenses or other optical components. Each of the microlenses may be configured to direct emission signals from an associated reaction site 814 to an associated light detector 836. Such microlenses may be used in addition to or as an alternative to the filter walls 840.

In some embodiments, the solid-state imager 832 and the base substrate 831 may be provided together as a previously constructed solid-state imaging device (e.g., CMOS chip). For example, the base substrate 831 may be a wafer of silicon and the solid-state imager 832 may be mounted thereon. The solid-state imager 832 includes a layer of semiconductor material (e.g., silicon) and the light detectors 836. In some embodiments, each light detector 836 is formed from a single pixel. In other embodiments, multiple pixels (e.g., 2, 3, 4, 5, 6, or more) may form a single light detector 836. In the illustrated embodiment, the light detector 836 pixels are photodiodes configured to detect light.

The solid-state imager 832 may include a dense array of light detectors 836 that are configured to detect activity indicative of a desired reaction from within or along the flow channel 818. In some embodiments, each light detector 836 has a detection area that is less than about 50 $\mu m^2$. In particular embodiments, the detection area is less than about 10 $\mu m^2$. In more particular embodiments, the detection area is about 2 $\mu m^2$. In such cases, the light detector 836 may constitute a single pixel. An average read noise of each pixel in a light detector 836 may be, for example, less than about 150 electrons. In some embodiments, the read noise may be less than about 50 electrons or less that about 25. In particular embodiments, the read noise may be less than about 5 electrons. The resolution of the array of light detectors 836 may be greater than about 0.5 megapixels (Mpixels). In more specific embodiments, the resolution may be greater than about 5 Mpixels and, more particularly, greater than about 10 Mpixels.

In some embodiments, the detection device 804 includes a microcircuit arrangement, such as the microcircuit arrangement described in U.S. Pat. No. 7,595,883, which is incorporated herein by reference in the entirety. More specifically, the detection device 804 may comprise an integrated circuit having a planar array of the light detectors 836. Circuitry formed within the detection device 804 may be configured for at least one of signal amplification, digitization, storage, and processing. The circuitry may collect and analyze the detected fluorescent light and generate data signals for communicating detection data to a bioassay system. The circuitry may also perform additional analog and/or digital signal processing in the detection device 804. The circuitry may include conductive pathways (e.g., wires) 850 that transmit the data signals to substrate layer 831. The conductive pathways 850 may continue from the substrate layer 831 to, for example, a computing system. The conductive pathways may include, for example, electrical contacts 854 or other form of a PCB, input/output (I/O) interface.

Experimental results were performed using a biosensor having features described herein, such as the embodiment shown and described with respect to FIG. 36. An assay was performed using a PhiX DNA control for SBS sequencing using reversible terminators. U.S. application Ser. No. 13/624,200, which is incorporated by reference in its entirety, describes methods and materials (e.g., dyes) that may be used with the biosensor. The protocol used to obtain the experimental results is similar to the PhiX protocol described in the "MiSeq System User Guide" from Illumina, Inc. (Part #15027617 Rev. G), January 2013, which is incorporated by reference in its entirety. The protocol was modified to include proprietary reagents that are provided in Miseq Reagent Kit v2. The modified protocol is described in greater detail in the "Preparing a PhiX Control for a Run on the MiSeq," (Part #15036175 Rev. A) (2013), which is incorporated by reference in its entirety.

In one operating session, about 875,123 clusters were produced within a flow channel and about 794,873 of these clusters were detectable (i.e., the detectable clusters emitted a sufficient amount of fluorescence to propagate through the filter layer of the biosensor and/or the emitted fluorescence was not negatively affected by crosstalk such that the clusters could not be differentiated). The number of sequencing cycles (e.g., incorporations of nucleotides to the sstDNA) was 151 cycles. The sequencing data from sixteen (16) tiles from the flowcell were analyzed.

Figure 37:
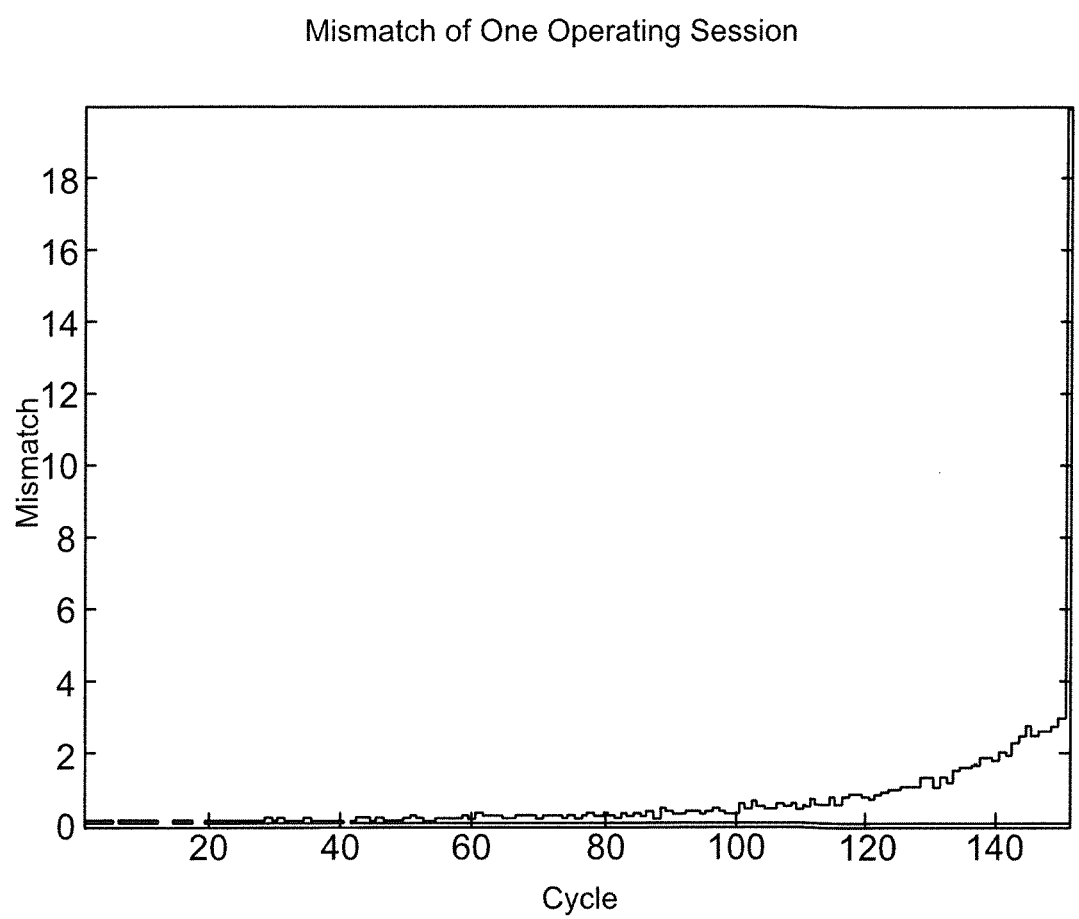
FIG. 37 shows mismatches on a cycle by cycle basis from a sequencing run, or one operational session.

Table 1 provided below provides data from the operating session described above, which include 151 cycles in the sequencing run or operational session. Table 1 includes the total number of kilobases detected during the operating session from all tiles. Table 1 also provides information provided, on average, for all tiles from the flowcell. Notably, the mismatch rate for clusters on the flowcell that provided optical signals that passed the filter layer was 0.94%+/−0.31%. FIG. 37 is a graph illustrating the mismatch rate per cycle for one of the tiles. Table 2 is also provided below and provides similar data for another operating session, which was performed before the operating session of Table 1. The mismatch rate in Table 2 is 1.31%+/−0.75%. Further, both Table 1 and 2 show that around 75% of the PhiX sequence aligned to the known PhiX sequence. As such, the biosensor was effective in detecting the optical signals to determine the sequence of the PhiX DNA during the SBS sequencing protocol.

TABLE 1

Lane Info Tile Mean ± SD for Lane 1

| Lane Yield (kbases) | Clusters (raw) | Clusters (PF) | 1st Cycle Int (PF) | % intensity after 20 cycles (PF) | % PF Clusters | % Align (PF) | Alignment Score (PF) | % Mismatch Rate (PF) |
|---|---|---|---|---|---|---|---|---|
| 120025 | 54695 ± 15628 | 49680 ± 17030 | 377.8 ± 141.8 | 96.4 ± 7.8 | 86.59 ± 17.86 | 75.02 ± 21.28 | 1.48 ± 0.38 | 0.94 ± 0.31 |

TABLE 2

Lane Info Tile Mean ± SD for Lane 1

| Lane Yield (kbases) | Clusters (raw) | Clusters (PF) | 1st Cycle Int (PF) | % intensity after 20 cycles (PF) | % PF Clusters | % Align (PF) | Alignment Score (PF) | % Mismatch Rate (PF) |
|---|---|---|---|---|---|---|---|---|
| 126656 | 45619 ± 10159 | 35819 ± 15403 | 1498.9 ± 447.0 | 88.3 ± 3.3 | 74.51 ± 25.86 | 73.89 ± 30.13 | 51.69 ± 14.63 | 1.31 ± 0.75 |

Accordingly, in one embodiment, a biosensor is provided, such as the biosensor 400. The biosensor may include a flow cell and a detection device that includes a plurality of stacked substrate layers. The detection device has a detector surface that is configured to support reaction sites. The stacked layers include a filter layer and a solid-state imager coupled to the filter layer. The filter layer includes filter walls and a light-absorbing material that is deposited between adjacent filter walls. The light-absorbing material is configured to prevent transmission of excitation light and permit transmission of emission signals, wherein the adjacent filter walls define a detection path therebetween through the corresponding light-absorbing material toward the solid-state imager. The filter walls may be configured to reflect the emission signals. The flow cell is mounted to the detector surface and defines a flow channel between at least one surface of the flow cell and the detection device. The at least one surface of the flow cell includes a material that permits transmission of the excitation light.

In one aspect, the solid-state imager includes a CMOS image sensor comprising an array of light detectors that are configured to detect the emission signals. In some embodiments, each of the light detectors has only a single pixel and wherein a ratio of the pixels to the detection paths defined by the filter walls is substantially one-to-one.

In another aspect, a length of the detection path is less than 10 microns.

In another aspect, the filter walls substantially define an image area along the detector surface. The reaction site being located within the image area and having a site area that is less than the image area.

In another aspect, the stacked layers are formed in a layer by layer manner using integrated circuit processing technologies.

In another aspect, the filter walls include first and second interior portions. The first interior portion extends in a direction from the reaction sites toward the solid-state imager. The second interior portion extends in a direction from the first interior portion toward the solid-state imager. The first and second interior portions have different reflectivity.

In another aspect, the filter walls include first and second interior portions. The first interior portion extends in a direction from the reaction sites toward the solid-state imager. The second interior portion extends in a direction from the first interior portion toward the solid-state imager. The second interior portion is configured to attenuate the emission signals from the reaction sites more than the first interior portion.

In another aspect, the detection path has a width that decreases as the detection path extends in a direction from the reaction sites toward the solid-state imager.

In another aspect, a ratio between a height of the filter walls and a width of the detection path that extends between the adjacent filter walls is at least 2.5:1.

In another aspect, the reaction sites include discrete metal regions on the detector surface.

In another aspect, the reaction sites include discrete clusters of nucleic acids.

In another embodiment, a method of analyzing signal data from a biosensor including a detection device is provided. The detection device includes an array of light detectors. Each of the light detectors is associated with at least one reaction site. The reaction sites include analytes-of-interest. The method includes (a) obtaining the signal data from the light detectors, the signal data including light scores that are based on an amount of light detected by the light detectors during a plurality of imaging events; (b) analyzing the light scores from a group of light detectors for each of the plurality of the imaging events; (c) determining respective crosstalk functions of the light detectors in the group, each of the crosstalk functions for a corresponding light detector being based on the amount of light detected by other light detectors in the group; and (d) analyzing the signal data for each of the imaging events using the crosstalk functions to determine characteristics of the analytes-of-interest.

In one aspect, the analyzing the light scores includes comparing the light scores of adjacent reaction sites to a predetermined score value to determine whether the adjacent reaction sites provided emission signals.

In another aspect, the crosstalk function is based on a number of adjacent reaction sites that provide emission signals and locations of the adjacent reaction sites that provide the emission signals.

In another aspect, the light scores correspond to voltage signals.

In another aspect, the light detected by the light sensors includes fluorescence emission signals. The fluorescent emission signals may be provided in response to an excitation event.

In another aspect, the imaging events occur according to a predetermined protocol.

In another aspect, the reaction sites include discrete metal regions on the detector surface.

In another aspect, the reaction sites include discrete clusters of nucleic acids.

In another embodiment, a system for biological and/or chemical analysis is provided. The system includes a receptacle that is configured to receive and establish electrical and fluidic connections with a biosensor. The biosensor is configured to have an array of light detectors in which each of the light detectors is associated with at least one reaction site located on a detector surface. The reaction sites are configured to include analytes-of-interest. The system also includes a fluidic control system for controlling a flow of fluid through the biosensor along the detector surface. The fluidic control system includes an upstream conduit for providing the fluid to the biosensor and a downstream conduit for removing the fluid. The system also includes an illumination system that is configured to direct excitation light toward the biosensor to illuminate the reaction sites, wherein at least some of the reaction sites provide emission signals when illuminated. The system also includes a system controller including an analysis module. The analysis module is configured to obtain signal data from the light detectors. The signal data includes light scores that are based on an amount of light detected by the light detectors during a plurality of imaging events. The system controller is also configured to analyze the light scores from a group of light detectors for each of the plurality of the imaging events. The system controller is also configured to determine respective crosstalk functions of the light detectors in the group. Each of the crosstalk functions for a corresponding light detector is based on the amount of light detected by other light detectors in the group. The system controller is also configured to analyze the signal data for each of the imaging events using the crosstalk functions to determine characteristics of the analytes-of-interest.

In one aspect, the analyzing the light scores includes comparing the light scores of adjacent reaction sites to a predetermined score value to determine whether the adjacent reaction sites provided emission signals.

In another aspect, the crosstalk function is based on a number of adjacent reaction sites that provided emission signals and locations of the adjacent reaction sites that provided the emission signals.

In another aspect, the emission signals are provided in response to an excitation event.

In another aspect, the system controller controls operation of the fluidic control system and the illumination system according to a predetermined protocol to provide the imaging events. The predetermined protocol may be a sequencing-by-synthesis protocol.

In another embodiment, a method of manufacturing a biosensor is provided. The method includes providing a solid-state imager including an array of light detectors. The method also includes coupling a filter layer to the solid-state imager. The filter layer includes filter walls and a light-absorbing material that is between adjacent filter walls. The light-absorbing material is configured to prevent transmission of excitation light and permit transmission of emission signals. The adjacent filter walls define a detection path therebetween through the corresponding light-absorbing material toward the solid-state imager. The filter walls are configured to reflect the emission signals. The method also includes coupling a passivation layer to the filter layer. The passivation layer has a detector surface. The method also includes positioning a flow cell over the detector surface. The flow cell defines a flow channel between at least one surface of the flow cell and the detector surface.

In one aspect, the coupling the filter layer operation includes coupling a substrate material to the solid-state imager and etching the substrate material to define chambers before the passivation layer is coupled.

In another aspect, the method further includes depositing a light-absorbing material into the chambers.

In another aspect, the method further comprises applying a coating to walls that define the chambers. The coating may be more reflective than material that defines the walls.

In another aspect, the method also includes preparing reaction sites along the detector surface.

In another aspect, the preparing operation includes locating the reaction sites at designated locations along the detector surface.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the specific components and processes described herein are intended to define the parameters of the various embodiments of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

What is claimed is:

1. A method of analyzing signal data from a biosensor including a detection device and a flow cell coupled to the detection device, the detection device and the flow cell defining a flow channel therebetween, the detection device including an array of light detectors, each of the light detectors being associated with at least one reaction site having analytes-of-interest, the reaction sites being located along a detector surface of the detection device that defines the flow channel, the method comprising:

illuminating the reaction sites with excitation light, the analytes-of-interest providing light emissions in response to the excitation light, the light emissions propagating through the flow channel and through the detector surface into the detection device;

detecting the light emissions by the light detectors, at least a portion of the light emissions detected by the light detectors including crosstalk light emissions from a non-associated reaction site;

obtaining the signal data from the light detectors, the signal data including light scores that are based on an amount of the light emissions detected by the light detectors during a plurality of imaging events;

analyzing the light scores from a group of light detectors of the array for each of the plurality of the imaging events;

determining respective crosstalk functions of the light detectors in the group from the analyzing the light scores from the group of light detectors of the array for each of the plurality of the imaging events, wherein each of the crosstalk functions for a corresponding light detector in the group is based on the amount of the light emissions detected by other light detectors in the group; and analyzing the signal data for each of the imaging events using the crosstalk functions to determine characteristics of the analytes-of-interest, wherein:

the detection device includes a filter layer extending between the detector surface and the light detectors, the filter layer including filter walls that are configured to reflect the light emissions toward the light detectors, a light-absorbing material being deposited within chambers that are defined between adjacent filter walls;

the adjacent filter walls define a detection path therebetween through the corresponding light-absorbing material toward the light detectors; and the filter walls include first and second interior portions, the first interior portion extending in a direction from the reaction sites toward the light detectors, the second interior portion extending in a direction from the first interior portion toward the light detectors.

2. The method of claim 1, wherein the determining respective crosstalk functions of the light detectors in the group includes:

for each imaging event in the plurality of imaging events:

determining a light score for each of the light detectors in the group from the imaging event;

identifying, as emitting, the at least one reaction site associated with the respective light detectors in the group having the light score for the respective imaging event greater than or equal to a predetermined score value;

identifying, as non-emitting, the reaction sites associated with the respective light detectors in the group having the light score for the respective imaging event less than the predetermined score value;

determining that the light score of the light detectors associated with non-emitting reaction sites is entirely from crosstalk emissions; and determining, for each of the non-emitting reaction sites, the number of adjacent reaction sites identified as emitting and the position of each adjacent reaction site relative to each non-emitting reaction site; and comparing the light scores of non-emitting reaction sites from the plurality of imaging events to determine crosstalk portions of the light scores provided by the adjacent reaction sites.

3. The method of claim 1, wherein each of the crosstalk functions of the light detectors in the group is based on a number of adjacent reaction sites that provided the light emissions and locations of the adjacent reaction sites that provided the light emissions.

4. The method of claim 1, wherein the analytes-of-interest are nucleic acids.

5. The method of claim 1, wherein the light scores correspond to voltage signals.

6. The method of claim 1, wherein the light emissions detected by the light sensors includes fluorescence emission signals.

7. The method of claim 1, wherein the reaction sites include discrete metal regions on the detector surface having discrete clusters of nucleic acids.

8. The method of claim 1, wherein the imaging events occur according to a predetermined protocol.

9. The method of claim 1, wherein the reaction sites include discrete metal regions on the detector surface.

10. The method of claim 1, wherein the reaction sites include discrete clusters of nucleic acids.

11. The method of claim 1, wherein a density of the reaction sites is at least one million reaction sites per square millimeter.

12. The method of claim 1, wherein the light detectors have detection areas that are less than about 50 µm².

13. The method of claim 1, wherein the analytes-of-interest are nucleic acids that form clusters at the reaction sites and the plurality of imaging events occur in accordance with a sequencing-by-synthesis protocol in which fluorescently-labeled nucleotides are incorporated into the nucleic acids prior to each imaging event.

14. The method of claim 1, wherein the detection device includes a passivation layer that defines the detector surface, the analytes-of-interest being immobilized to the detector surface and exposed to the flow channel, the light emissions propagating through the passivation layer toward the light detectors.

15. The method of claim 14, wherein the passivation layer extends between the filter layer and the flow channel, and at least some of the crosstalk light emissions propagate through the flow channel and the passivation layer and over one or more of the filter walls.

16. The method of claim 15, wherein each of the reaction sites corresponding to the group of light detectors is located within a site area along the detector surface, the site areas having shapes defined by the filter walls, wherein the reaction sites have different locations within the site areas.

17. The method of claim 14, wherein: the passivation layer extends between the filter layer and the flow channel; the light-absorbing material filters the excitation light; and the crosstalk light emissions propagate through the flow channel, the passivation layer, and the light-absorbing material to the light detectors.

18. The method of claim 1, wherein
the second interior portion is to attenuate the light emissions from the reaction sites more than the first interior portion.

19. The method of claim 1 wherein:
the first interior portion is coated with a reflective coating material and the second interior portion is not coated or is coated with a different material; and
the light emissions from the reaction sites that are reflected by the coating are less attenuated than the light emissions that are reflected by the second interior portion of the filter walls.

20. The method of claim 1 wherein:
a width for each of the detection paths decreases as the detection path extends toward the light detector;
a thickness of the filter wall begins to increase as the filter wall transitions from the first interior portion to the second interior portion; and
as the thickness of the filter wall increases, the width for the respective detection path decreases.

* * * * *